(12) United States Patent
Oku et al.

(10) Patent No.: US 8,071,842 B2
(45) Date of Patent: Dec. 6, 2011

(54) METHOD OF CONSTRUCTING NOVEL HIGHER PLANT AND METHOD OF PROMOTING THE GROWTH OF HIGHER PLANT

(75) Inventors: Tadatake Oku, Tokyo (JP); Toshiyuki Nishio, Tokyo (JP); Ryu Kawachi, Tokyo (JP); Hirotaka Chida, Fujisawa (JP); Aiko Nakazawa, Kawasaki (JP)

(73) Assignee: Nihon University, Tokyo (JP)

( * ) Notice: Subject to any disclaimer, the term of this patent is extended or adjusted under 35 U.S.C. 154(b) by 870 days.

(21) Appl. No.: 11/883,240

(22) PCT Filed: Feb. 1, 2006

(86) PCT No.: PCT/JP2006/302104
§ 371 (c)(1),
(2), (4) Date: Jul. 26, 2007

(87) PCT Pub. No.: WO2006/082992
PCT Pub. Date: Aug. 10, 2006

(65) Prior Publication Data
US 2008/0282428 A1  Nov. 13, 2008

(30) Foreign Application Priority Data
Feb. 2, 2005 (JP) ................................. 2005-027012

(51) Int. Cl.
C12N 15/30 (2006.01)
C12N 15/52 (2006.01)
C12N 15/82 (2006.01)

(52) U.S. Cl. ........ 800/284; 800/288; 800/290; 800/298; 800/317; 800/320

(58) Field of Classification Search .......... None
See application file for complete search history.

(56) References Cited

FOREIGN PATENT DOCUMENTS
JP     2002-218979 A     8/2002
WO    WO-02/59339 A1    1/2002

OTHER PUBLICATIONS

Nakazawa, A. et al. Japan Society for Biosciences, Biotechnology and Agrochemistry (2004): poster abstract 3c04p07 pp. 302.*
Kieselbach T. et al. FEBS Letters (2000); vol. 480 pp. 271-276.*
Oku et al. CYC_PORYE; Accession Q8WKJ8, Submitted Mar. 2002.*
Chida, H. et al. Plant Cell Physiol., 2007: vol. 48, No. 7; pp. 948-957.*
Gupta et al. "Functional relationship of cytochrome c6 and plastocyanin in *Arabidopsis*" Nature (London), vol. 417, No. 6888, May 30, 2002, pp. 567-571, XP 002473091.
Weigel et al. "Plastocyanin is indispensable for photosynthetic electron flow in *Arabidopsis thaliana*." Journal of Biological Chemistry, vol. 278, No. 33, Aug. 15, 2003, pp. 31286-31289, XP 002473092.
Wastl el al. "Redox properties of *Arabidopsis* cytochrome c6 are independent of the loop extension specific to higher plants." Biochimica Et Biophysica Acta. Bioenergetics, Amsterdam, Nl., vol. 1657, No. 2-3, Jul. 9, 2004, pp. 115-120, XP 004518645.
Nakazawa et al., "*Arabidopsis thaliana* eno Sorui Cytochrome $C_6$ Idenshi Donyukei no Kento," Nendo Nippon Nogei Kagakukai Taikai Koen Yoshishu, 2004, pp. 302.
Weisbeek et al., "Import of proteins into the chloroplast lumen," J. Cell. Sci. Suppl., vol. 11, 1989, pp. 199-223.
Merchant et al., "Posttranslational assembly of photosynthetic metalloproteins," Annu. Rev. Plant Physiol. Plant Mol. Biol., vol. 49, 1998, pp. 25-51.
Lefebvre et al., "Increased Sedoheptulose-1,7-Bisphosphatase Activity in Transgenic Tobacco Plants Stimulates Photosynthesis and Growth from an Early Stage in Development," Dept. Biol. Sci., Plant Physiology, vol. 138, 2005, pp. 451-460.

* cited by examiner

*Primary Examiner* — Russell Kallis
(74) *Attorney, Agent, or Firm* — Birch, Stewart, Kolasch & Birch, LLP

(57) ABSTRACT

The present invention provides a method of producing a higher plant having cytochrome $c_6$ in the thylakoid space of chloroplast, which is characterized in that it comprises introducing a gene encoding a fused protein formed by adding a signal peptide consisting of 50 to 80 amino acid residues to a cytochrome $c_6$ protein into the genome of a higher plant.

7 Claims, 19 Drawing Sheets
(13 of 19 Drawing Sheet(s) Filed in Color)

Lane

I : 100 bp DNA Ladder

II : PCR product (Cyt c₆ mature peptide)

▲ indicates the boundary between a signal peptide and a mature protein region.

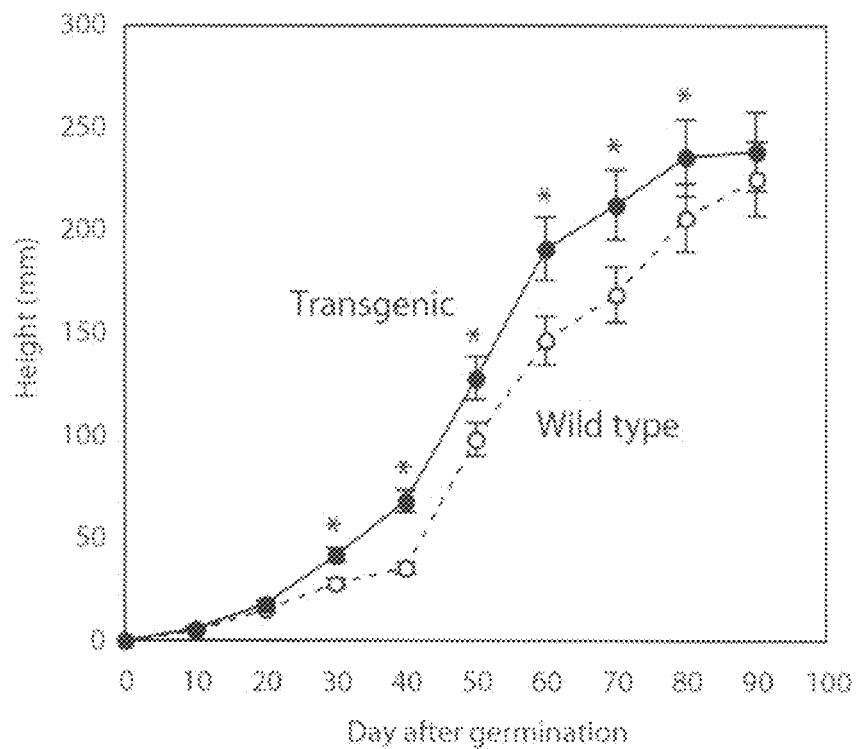
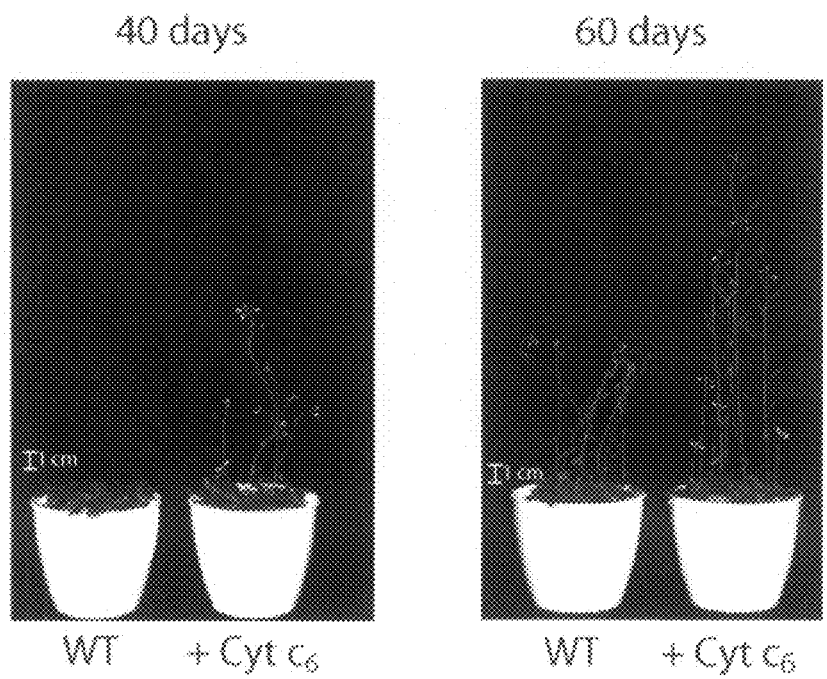
Fig. 11

Fig. 12
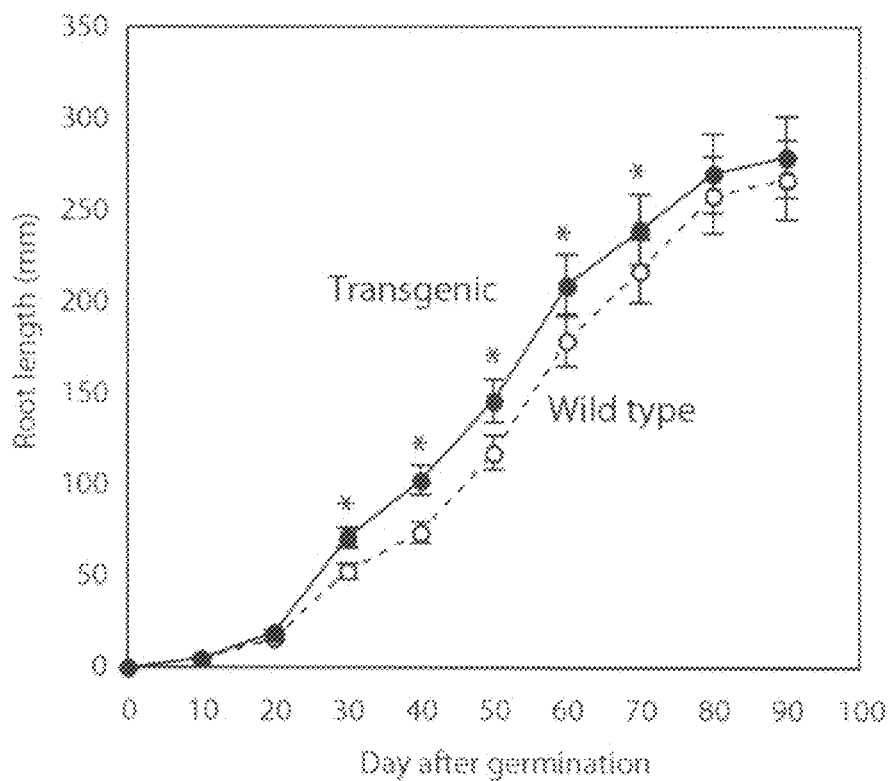
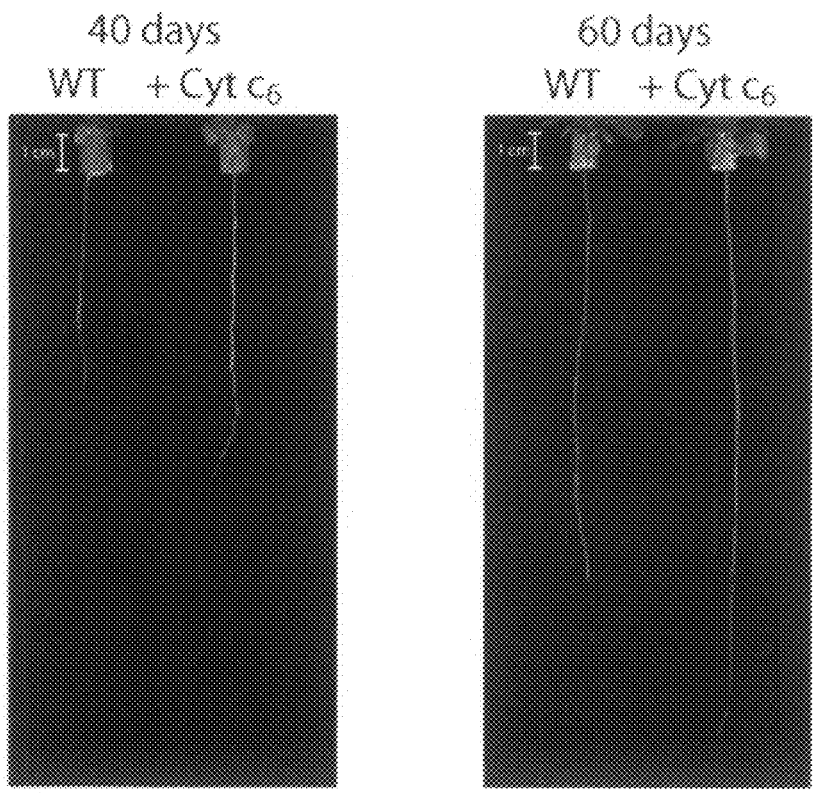

Fig. 13
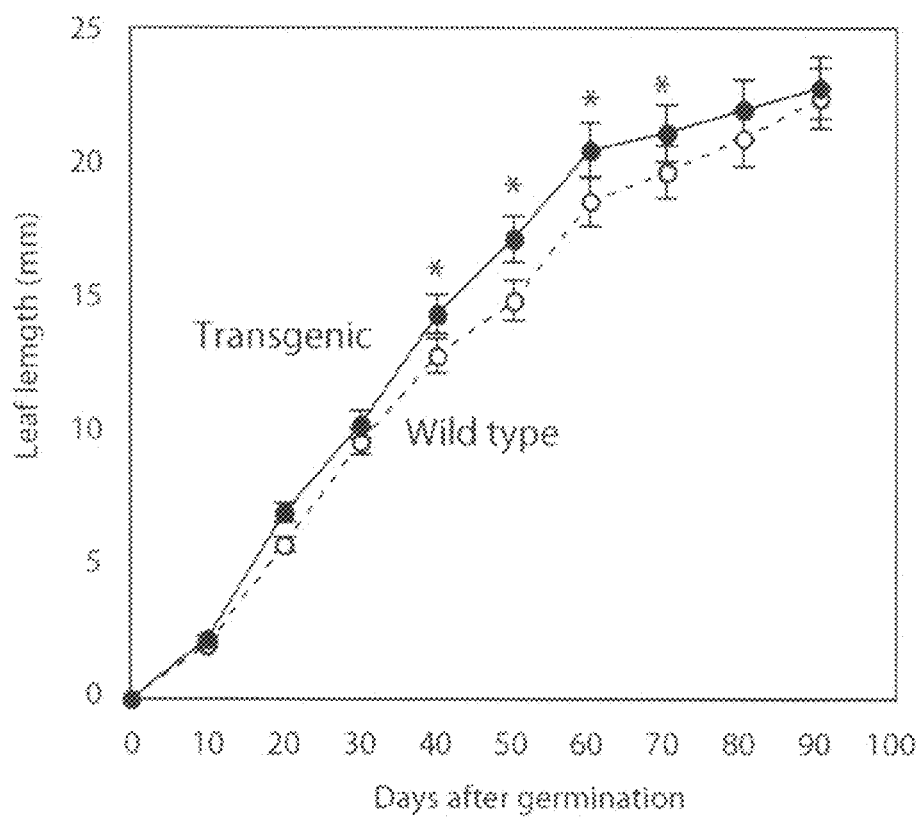
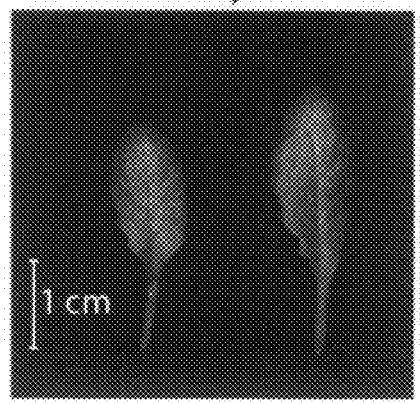
40 days
WT    + Cyt c$_6$
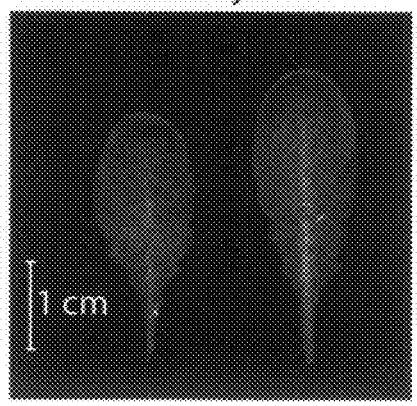
60 days
WT    + Cyt c$_6$

```
SEQUENCE LISTING

<160> NUMBER OF SEQ ID NOS: 16

<210> SEQ ID NO 1
<211> LENGTH: 258
<212> TYPE: DNA
<213> ORGANISM: Porphyra yezoensis
<220> FEATURE:
<221> NAME/KEY: CDS
<222> LOCATION: (1)..(258)

<400> SEQUENCE: 1 gca gat cta gat aat gga gaa aaa gtt ttt tct gct aat tgt gca gca        48
Ala Asp Leu Asp Asn Gly Glu Lys Val Phe Ser Ala Asn Cys Ala Ala
1               5                  10                  15 tgt cat gct ggc ggt aat aac gcc att atg cca gat aaa acc tta aaa        96
Cys His Ala Gly Gly Asn Asn Ala Ile Met Pro Asp Lys Thr Leu Lys
            20                  25                  30 aaa gat gta ctt gaa gct aat agt atg aat act att gat gct att act       144
Lys Asp Val Leu Glu Ala Asn Ser Met Asn Thr Ile Asp Ala Ile Thr
        35                  40                  45 tat caa gta caa aat ggt aaa aat gcc atg cct gct ttc gga ggt aga       192
Tyr Gln Val Gln Asn Gly Lys Asn Ala Met Pro Ala Phe Gly Gly Arg
    50                  55                  60 ctg gtt gat gaa gat att gaa gat gca gca aat tat gta tta tct caa       240
Leu Val Asp Glu Asp Ile Glu Asp Ala Ala Asn Tyr Val Leu Ser Gln
65                  70                  75                  80 tct gaa aaa ggt tgg taa                                               258
Ser Glu Lys Gly Trp
                85

<210> SEQ ID NO 2
<211> LENGTH: 85
<212> TYPE: PRT
<213> ORGANISM: Porphyra yezoensis

<400> SEQUENCE: 2

Ala Asp Leu Asp Asn Gly Glu Lys Val Phe Ser Ala Asn Cys Ala Ala
1               5                  10                  15

Cys His Ala Gly Gly Asn Asn Ala Ile Met Pro Asp Lys Thr Leu Lys
            20                  25                  30
```

```
Lys Asp Val Leu Glu Ala Asn Ser Met Asn Thr Ile Asp Ala Ile Thr
         35                  40                  45

Tyr Gln Val Gln Asn Gly Lys Asn Ala Met Pro Ala Phe Gly Gly Arg
 50                  55                  60

Leu Val Asp Glu Asp Ile Glu Asp Ala Ala Asn Tyr Val Leu Ser Gln
 65                  70                  75                  80

Ser Glu Lys Gly Trp
             85

<210> SEQ ID NO 3
<211> LENGTH: 216
<212> TYPE: DNA
<213> ORGANISM: Porphyra yezoensis
<220> FEATURE:
<221> NAME/KEY: CDS
<222> LOCATION: (1)..(216)

<400> SEQUENCE: 3 atg gcc gca att aca tca gct acc gtc acc atc cct tct ttc acc ggc        48
Met Ala Ala Ile Thr Ser Ala Thr Val Thr Ile Pro Ser Phe Thr Gly
 1               5                  10                  15 cta aag ctc gcc gtc agc tca aaa cct aag aca tta tcc acc atc agt        96
Leu Lys Leu Ala Val Ser Ser Lys Pro Lys Thr Leu Ser Thr Ile Ser
             20                  25                  30 aga tcc tct tcc gcc acc agg gcg cca cct aag ctc gct ttg aag tcc       144
Arg Ser Ser Ser Ala Thr Arg Ala Pro Pro Lys Leu Ala Leu Lys Ser
         35                  40                  45 tct ttg aag gat ttc ggt gtc atc gca gtg gca aca gca gct tcg atc       192
Ser Leu Lys Asp Phe Gly Val Ile Ala Val Ala Thr Ala Ala Ser Ile
 50                  55                  60 gtt tta gct gga aat gcg atg gcc                                        216
Val Leu Ala Gly Asn Ala Met Ala
 65                  70

<210> SEQ ID NO 4
<211> LENGTH: 72
<212> TYPE: PRT
<213> ORGANISM: Porphyra yezoensis

<400> SEQUENCE: 4

Met Ala Ala Ile Thr Ser Ala Thr Val Thr Ile Pro Ser Phe Thr Gly
 1               5                  10                  15

Leu Lys Leu Ala Val Ser Ser Lys Pro Lys Thr Leu Ser Thr Ile Ser
             20                  25                  30

Arg Ser Ser Ser Ala Thr Arg Ala Pro Pro Lys Leu Ala Leu Lys Ser
         35                  40                  45

Ser Leu Lys Asp Phe Gly Val Ile Ala Val Ala Thr Ala Ala Ser Ile
 50                  55                  60

Val Leu Ala Gly Asn Ala Met Ala
 65                  70

<210> SEQ ID NO 5
<211> LENGTH: 474
<212> TYPE: DNA
<213> ORGANISM: Porphyra yezoensis
<220> FEATURE:
<221> NAME/KEY: CDS
<222> LOCATION: (1)..(474)

<400> SEQUENCE: 5 atg gcc gca att aca tca gct acc gtc acc atc cct tct ttc acc ggc        48
Met Ala Ala Ile Thr Ser Ala Thr Val Thr Ile Pro Ser Phe Thr Gly
 1               5                  10                  15
```

```
cta aag ctc gcc gtc agc tca aaa cct aag aca tta tcc acc atc agt       96
Leu Lys Leu Ala Val Ser Ser Lys Pro Lys Thr Leu Ser Thr Ile Ser
         20                  25                  30 aga tcc tct tcc gcc acc agg gcg cca cct aag ctc gct ttg aag tcc      144
Arg Ser Ser Ser Ala Thr Arg Ala Pro Pro Lys Leu Ala Leu Lys Ser
             35                  40                  45 tct ttg aag gat ttc ggt gtc atc gca gtg gca aca gca gct tcg atc      192
Ser Leu Lys Asp Phe Gly Val Ile Ala Val Ala Thr Ala Ala Ser Ile
 50                  55                  60 gtt tta gct gga aat gcg atg gct gca gat cta gat aat gga gaa aaa      240
Val Leu Ala Gly Asn Ala Met Ala Ala Asp Leu Asp Asn Gly Glu Lys
 65                  70                  75                  80 gtt ttt tct gct aat tgt gca gca tgt cat gct ggc ggt aat aac gcc      288
Val Phe Ser Ala Asn Cys Ala Ala Cys His Ala Gly Gly Asn Asn Ala
             85                  90                  95 att atg cca gat aaa acc tta aaa aaa gat gta ctt gaa gct aat agt      336
Ile Met Pro Asp Lys Thr Leu Lys Lys Asp Val Leu Glu Ala Asn Ser
            100                 105                 110 atg aat act att gat gct att act tat caa gta caa aat ggt aaa aat      384
Met Asn Thr Ile Asp Ala Ile Thr Tyr Gln Val Gln Asn Gly Lys Asn
        115                 120                 125 gcc atg cct gct ttc gga ggt aga ctg gtt gat gaa gat att gaa gat      432
Ala Met Pro Ala Phe Gly Gly Arg Leu Val Asp Glu Asp Ile Glu Asp
    130                 135                 140 gca gca aat tat gta tta tct caa tct gaa aaa ggt tgg taa              474
Ala Ala Asn Tyr Val Leu Ser Gln Ser Glu Lys Gly Trp
145                 150                 155

<210> SEQ ID NO 6
<211> LENGTH: 157
<212> TYPE: PRT
<213> ORGANISM: Porphyra yezoensis

<400> SEQUENCE: 6

Met Ala Ala Ile Thr Ser Ala Thr Val Thr Ile Pro Ser Phe Thr Gly
 1               5                  10                  15

Leu Lys Leu Ala Val Ser Ser Lys Pro Lys Thr Leu Ser Thr Ile Ser
             20                  25                  30

Arg Ser Ser Ser Ala Thr Arg Ala Pro Pro Lys Leu Ala Leu Lys Ser
         35                  40                  45

Ser Leu Lys Asp Phe Gly Val Ile Ala Val Ala Thr Ala Ala Ser Ile
     50                  55                  60

Val Leu Ala Gly Asn Ala Met Ala Ala Asp Leu Asp Asn Gly Glu Lys
 65                  70                  75                  80

Val Phe Ser Ala Asn Cys Ala Ala Cys His Ala Gly Gly Asn Asn Ala
                 85                  90                  95

Ile Met Pro Asp Lys Thr Leu Lys Lys Asp Val Leu Glu Ala Asn Ser
            100                 105                 110

Met Asn Thr Ile Asp Ala Ile Thr Tyr Gln Val Gln Asn Gly Lys Asn
        115                 120                 125

Ala Met Pro Ala Phe Gly Gly Arg Leu Val Asp Glu Asp Ile Glu Asp
    130                 135                 140

Ala Ala Asn Tyr Val Leu Ser Gln Ser Glu Lys Gly Trp
145                 150                 155

<210> SEQ ID NO 7
<211> LENGTH: 30
<212> TYPE: DNA
<213> ORGANISM: Artificial Sequence
```

-continued

<220> FEATURE:
<223> OTHER INFORMATION: Synthetic primer

<400> SEQUENCE: 7
ggagctctta ccaaccttt tcagattgag                                      30

<210> SEQ ID NO 8
<211> LENGTH: 29
<212> TYPE: DNA
<213> ORGANISM: Artificial Sequence
<220> FEATURE:
<223> OTHER INFORMATION: Synthetic primer

<400> SEQUENCE: 8
ccgcggagac gttaaattga agaagaagc                                      29

<210> SEQ ID NO 9
<211> LENGTH: 24
<212> TYPE: DNA
<213> ORGANISM: Artificial Sequence
<220> FEATURE:
<223> OTHER INFORMATION: Synthetic primer

<400> SEQUENCE: 9
cgccagggtt ttcccagtca cgac                                           24

<210> SEQ ID NO 10
<211> LENGTH: 24
<212> TYPE: DNA
<213> ORGANISM: Artificial Sequence
<220> FEATURE:
<223> OTHER INFORMATION: Synthetic primer

<400> SEQUENCE: 10
gagcggataa caatttcaca cagg                                           24

<210> SEQ ID NO 11
<211> LENGTH: 31
<212> TYPE: DNA
<213> ORGANISM: Artificial Sequence
<220> FEATURE:
<223> OTHER INFORMATION: Synthetic primer

<400> SEQUENCE: 11
ggatccatgg ccgcaattac atcagctacc g                                   31

<210> SEQ ID NO 12
<211> LENGTH: 10
<212> TYPE: PRT
<213> ORGANISM: Porphyra yezoensis

<400> SEQUENCE: 12

Ala Asp Leu Asp Asn Gly Glu Lys Val Phe
1               5                   10

<210> SEQ ID NO 13
<211> LENGTH: 360
<212> TYPE: DNA
<213> ORGANISM: Porphyra yezoensis

<400> SEQUENCE: 13
aaaaaggaga cgttaaattg aagaagaagc tttcagttct tttcactgtt tttagttttt    60
ttgtaatagg tttcgcacaa attgcttttg ctgcagatct agataatgga gaaaagtttt   120
tttctgctaa ttgtgcagca tgtcatgctg gcggtaataa cgccattatg ccagataaaa   180

```
ccttaaaaaa agatgtactt gaagctaata gtatgaatac tattgatgct attacttatc    240
aagtacaaaa tggtaaaaat gccatgcctg ctttcggagg tagactggtt gatgaagata    300
ttgaagatgc agcaaattat gtattatctc aatctgaaaa aggttggtaa ttatacttga    360
```

<210> SEQ ID NO 14
<211> LENGTH: 110
<212> TYPE: PRT
<213> ORGANISM: Porphyra yezoensis

<400> SEQUENCE: 14

```
Met Lys Lys Lys Leu Ser Val Leu Phe Thr Val Phe Ser Phe Phe Val
1               5                   10                  15

Ile Gly Phe Ala Gln Ile Ala Phe Ala Ala Asp Leu Asp Asn Gly Glu
            20                  25                  30

Lys Val Phe Ser Ala Asn Cys Ala Ala Cys His Ala Gly Gly Asn Asn
        35                  40                  45

Ala Ile Met Pro Asp Lys Thr Leu Lys Lys Asp Val Leu Glu Ala Asn
    50                  55                  60

Ser Met Asn Thr Ile Asp Ala Ile Thr Tyr Gln Val Gln Asn Gly Lys
65                  70                  75                  80

Asn Ala Met Pro Ala Phe Gly Gly Arg Leu Val Asp Glu Asp Ile Glu
                85                  90                  95

Asp Ala Ala Asn Tyr Val Leu Ser Gln Ser Glu Lys Gly Trp
            100                 105                 110
```

<210> SEQ ID NO 15
<211> LENGTH: 487
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (7)..(480)

<400> SEQUENCE: 15

```
ggatcc atg gcc gca att aca tca gct acc gtc acc atc cct tct ttc        48
       Met Ala Ala Ile Thr Ser Ala Thr Val Thr Ile Pro Ser Phe
       1               5                   10 acc ggc cta aag ctc gcc gtc agc tca aaa cct aag aca tta tcc acc       96
Thr Gly Leu Lys Leu Ala Val Ser Ser Lys Pro Lys Thr Leu Ser Thr
15                  20                  25                  30 atc agt aga tcc act tcc gcc acc agg gcg cca cct aag ctc gct ttg      144
Ile Ser Arg Ser Thr Ser Ala Thr Arg Ala Pro Pro Lys Leu Ala Leu
                35                  40                  45 aag tcc tct ttg aag gat ttc ggt gtc atc gca gtg gca aca gca gct      192
Lys Ser Ser Leu Lys Asp Phe Gly Val Ile Ala Val Ala Thr Ala Ala
            50                  55                  60 tcg atc gtt tta gct gga aat gcg atg gct gca gat cta gat aat gga      240
Ser Ile Val Leu Ala Gly Asn Ala Met Ala Ala Asp Leu Asp Asn Gly
        65                  70                  75 gaa aaa gtt ttt tct gct aat tgt gca gca tgt cat gct ggc ggt aat      288
Glu Lys Val Phe Ser Ala Asn Cys Ala Ala Cys His Ala Gly Gly Asn
    80                  85                  90 aac gcc att atg cca gat aaa acc tta aaa aaa gat gta ctt gaa gct      336
Asn Ala Ile Met Pro Asp Lys Thr Leu Lys Lys Asp Val Leu Glu Ala
95                  100                 105                 110 aat agt atg aat act att gat gct att act tat caa gta caa aat ggt      384
Asn Ser Met Asn Thr Ile Asp Ala Ile Thr Tyr Gln Val Gln Asn Gly
                115                 120                 125
```

-continued

```
aaa aat gcc atg cct gct ttc gga ggt aga ctg gtt gat gaa gat att    432
Lys Asn Ala Met Pro Ala Phe Gly Gly Arg Leu Val Asp Glu Asp Ile
            130                 135                 140 gaa gat gca gca aat tat gta tta tct caa tct gaa aaa ggt tgg taa    480
Glu Asp Ala Ala Asn Tyr Val Leu Ser Gln Ser Glu Lys Gly Trp
        145                 150                 155 gagctcc                                                             487
```

<210> SEQ ID NO 16
<211> LENGTH: 157
<212> TYPE: PRT
<213> ORGANISM: Artificial Sequence
<220> FEATURE:
<223> OTHER INFORMATION: Synthetic protein

<400> SEQUENCE: 16

```
Met Ala Ala Ile Thr Ser Ala Thr Val Thr Ile Pro Ser Phe Thr Gly
1               5                   10                  15

Leu Lys Leu Ala Val Ser Ser Lys Pro Lys Thr Leu Ser Thr Ile Ser
            20                  25                  30

Arg Ser Thr Ser Ala Thr Arg Ala Pro Pro Lys Leu Ala Leu Lys Ser
        35                  40                  45

Ser Leu Lys Asp Phe Gly Val Ile Ala Val Ala Thr Ala Ala Ser Ile
50                  55                  60

Val Leu Ala Gly Asn Ala Met Ala Ala Asp Leu Asp Asn Gly Glu Lys
65                  70                  75                  80

Val Phe Ser Ala Asn Cys Ala Ala Cys His Ala Gly Gly Asn Asn Ala
                85                  90                  95

Ile Met Pro Asp Lys Thr Leu Lys Lys Asp Val Leu Glu Ala Asn Ser
            100                 105                 110

Met Asn Thr Ile Asp Ala Ile Thr Tyr Gln Val Gln Asn Gly Lys Asn
        115                 120                 125

Ala Met Pro Ala Phe Gly Gly Arg Leu Val Asp Glu Asp Ile Glu Asp
    130                 135                 140

Ala Ala Asn Tyr Val Leu Ser Gln Ser Glu Lys Gly Trp
145                 150                 155
```

US 8,071,842 B2

METHOD OF CONSTRUCTING NOVEL HIGHER PLANT AND METHOD OF PROMOTING THE GROWTH OF HIGHER PLANT

TECHNICAL FIELD

The present invention relates to a method of producing a novel higher plant having cytochrome $c_6$ in the thylakoid space of chloroplast, and a method of promoting the growth of a higher plant by allowing cytochrome $c_6$ in the aforementioned thylakoid space of chloroplast or a method of promoting the ability of a higher plant to fix carbon.

BACKGROUND ART

As a technique of promoting the growth of a so-called higher plant such as a land plant, a photosynthetic dark reaction (Calvin-Benson cycle), which involves the enhancement of the activity of enzyme such as ribulosebisphosphate carboxylase, has previously been reported. Specifically, a technique of enlarging leaves by introducing a related enzyme gene into such a higher plant has been reported (Shigeoka et al., Nature biotechnology, 19, 965-969 (2001)). However, it has been extremely difficult to apply such techniques to various types of higher plants.

Cytochrome $c_6$ is an electron transfer protein in a photosynthetic light reaction, and in general, it exists only in several types of algae (blue-green algae, etc.) It has been known that cytochrome $c_6$ has excellent electron-transferring ability (that is, its oxidation-reduction potential is high) (FIG. 1). Thus, it has been strongly desired that a general-purpose technique of allowing cytochrome $c_6$ to express and function in the chloroplast (more in detail, in the thylakoid space) of various types of higher plants, so as to improve photosynthetic ability, be developed.

By the way, examples of a technique of allowing cytochrome $c_6$ to express in a cell include those described in publications such as F. P. Molina-Heredia et al., Biochem. Biophys. Res. Commun., 243, 302-306 (1998); T. Satoh et al., FEBS lett., 531, 543-547 (2002); R. Gupta et al., Nature, 417, 567-571 (2002); and D. R. Hickey et al., Gene, 105, 73-81 (1991). However, in all of these techniques, host cells have not been those of higher plants, and cells of *Escherichia coli*, yeast, or blue-green algae, have been used just for simple purposes, such as mass-production of the aforementioned cytochrome $c_6$ or a protein associated therewith, or the function analysis thereof. Hence, such techniques have been included in the gene expression method, which has been commonly carried out by persons skilled in the art.

There have been no reports regarding that cytochrome $c_6$ is allowed to function as an electron carrier in a photosynthetic light reaction in higher plants, namely, regarding that cytochrome $c_6$ is successfully allowed to exist in the thylakoid space of the chloroplast of a higher plant cell. Thus, such a technique has been considered extremely difficult.

DISCLOSURE OF THE INVENTION

It is an object of the present invention to provide a method of producing a novel higher plant having cytochrome $c_6$ in the thylakoid space of chloroplast, and eventually, to provide a method of promoting the growth of a higher plant, a method of promoting the synthesis of at least one selected from the group consisting of ATP, NADPH, a starch and a protein, and a method of promoting carbon fixation.

The present inventor has conducted intensive studies directed towards achieving the aforementioned object. As a result, the inventor has found that if a cytochrome $c_6$ protein gene, to which a specific signal peptide has been added, is introduced into the genomic DNA of a higher plant so as to allow the gene to express therein, it becomes possible to transfer cytochrome $c_6$ into (allow cytochrome $c_6$ to pass through) the chloroplast envelope and thylakoid membrane of the above higher plant, which had conventionally been considered to be impossible, thereby completing the present invention.

That is to say, the present invention has the following features (1) to (15).

(1) A method of producing a higher plant having cytochrome $c_6$ in the thylakoid space of chloroplast, which is characterized in that it comprises introducing a gene encoding a fused protein formed by adding a signal peptide consisting of 50 to 80 amino acid residues to a cytochrome $c_6$ protein into the genome of a higher plant.

(2) A method of promoting the growth of a higher plant, which is characterized in that it comprises introducing a gene encoding a fused protein formed by adding a signal peptide consisting of 50 to 80 amino acid residues to a cytochrome $c_6$ protein into the genome of a higher plant, so as to allow the gene to express therein, and allowing cytochrome $c_6$ to exist in the thylakoid space of chloroplast.

(3) A method of promoting the synthesis of at least one selected from the group consisting of the ATP, NADPH, starch, and protein of a higher plant, which is characterized in that it comprises introducing a gene encoding a fused protein formed by adding a signal peptide consisting of 50 to 80 amino acid residues to a cytochrome $c_6$ protein into the genome of a higher plant, so as to allow the gene to express therein, and allowing cytochrome $c_6$ to exist in the thylakoid space of chloroplast.

(4) A method of promoting carbon fixation by a higher plant, which is characterized in that it comprises introducing a gene encoding a fused protein formed by adding a signal peptide consisting of 50 to 80 amino acid residues to a cytochrome $c_6$ protein into the genome of a higher plant, so as to allow the gene to express therein, and allowing cytochrome $c_6$ to exist in the thylakoid space of chloroplast.

In the method according to any one of (1) to (4) above, the above-described fused protein may be the protein described in the following (a), (b), (c), or (d):

(a) a protein having the amino acid sequence as shown in SEQ ID NO: 6;

(b) a protein, which has an amino acid sequence comprising a deletion, substitution, or addition of one or several amino acids with respect to an amino acid sequence portion corresponding to the above-described signal peptide in the amino acid sequence as shown in SEQ ID NO: 6, and which has ability to pass through the chloroplast envelope and thylakoid membrane of a higher plant;

(c) a protein, which has an amino acid sequence comprising a deletion, substitution, or addition of one or several amino acids with respect to an amino acid sequence portion corresponding to the above-described cytochrome $c_6$ protein in the amino acid sequence as shown in SEQ ID NO: 6, and which has ability to transfer electrons; and (d) a protein, which has an amino acid sequence comprising a deletion, substitution, or addition of one or several amino acids with respect to each of an amino acid sequence portion corresponding to the above-described signal peptide and an amino acid sequence portion corresponding to the above-described cytochrome $c_6$ protein in the amino acid sequence as shown in SEQ ID NO: 6, and which has ability to pass through the chloroplast envelope and thylakoid membrane of a higher plant and ability to transfer electrons.

In addition, in the method according to any one of (1) to (4) above, the above-described gene may be a gene comprising the DNA described in the following (a) or (b):
(a) DNA having the nucleotide sequence as shown in SEQ ID NO: 5; and
(b) DNA, which hybridizes with DNA having a nucleotide sequence complementary to the DNA having the nucleotide sequence as shown in SEQ ID NO: 5 under stringent conditions, and which encodes a protein having ability to pass through the chloroplast envelope and thylakoid membrane of a higher plant and ability to transfer electrons.
(5) A fused protein, which is formed by adding a signal peptide consisting of 50 to 80 amino acid residues to a cytochrome $c_6$ protein.

The fused protein according to (5) above may be the protein described in the following (a), (b), (c), or (d):
(a) a protein having the amino acid sequence as shown in SEQ ID NO: 6;
(b) a protein, which has an amino acid sequence comprising a deletion, substitution, or addition of one or several amino acids with respect to an amino acid sequence portion corresponding to the above-described signal peptide in the amino acid sequence as shown in SEQ ID NO: 6, and which has ability to pass through the chloroplast envelope and thylakoid membrane of a higher plant;
(c) a protein, which has an amino acid sequence comprising a deletion, substitution, or addition of one or several amino acids with respect to an amino acid sequence portion corresponding to the above-described cytochrome $c_6$ protein in the amino acid sequence as shown in SEQ ID NO: 6, and which has ability to transfer electrons; and
(d) a protein, which has an amino acid sequence comprising a deletion, substitution, or addition of one or several amino acids with respect to each of an amino acid sequence portion corresponding to the above-described signal peptide and an amino acid sequence portion corresponding to the above-described cytochrome $c_6$ protein in the amino acid sequence as shown in SEQ ID NO: 6, and which has ability to pass through the chloroplast envelope and thylakoid membrane of a higher plant and ability to transfer electrons.
(6) A gene, which encodes the fused protein according to (5) above.
(7) A gene, which comprises the DNA described in the following (a) or (b):
(a) DNA having the nucleotide sequence as shown in SEQ ID NO: 5; and
(b) DNA, which hybridizes with DNA having a nucleotide sequence complementary to the DNA having the nucleotide sequence as shown in SEQ ID NO: 5 under stringent conditions, and which encodes a protein having ability to pass through the chloroplast envelope and thylakoid membrane of a higher plant and ability to transfer electrons.
(8) A recombinant vector, which comprises the gene according to (6) or (7) above.
(9) A transformant, which is obtained by introducing the recombinant vector according to (8) above into a host.

The transformant according to (9) above may be a transformant wherein the host is a microorganism belonging to genus *Agrobacterium*.
(10) A transgenic higher plant, which is obtained by introducing the gene according to (6) or (7) above into the plant genome thereof.

The transgenic higher plant according to (10) above preferably has cytochrome $c_6$ in the thylakoid space of chloroplast in a plant cell thereof.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 11 is a view showing a change in the height of a wild type (○) and in the height of transgenic *A. thaliana* (●), which has been observed with the course of growing days. Each value in the graph indicates average±S.D. (standard deviation) (n=20). The asterisk (*) indicates a value having a significant difference at 5% significance level.

FIG. 12 is a view showing a change in the root length of a wild type (○) and in the root length of transgenic *A. thaliana* (●), which has been observed with the course of growing days. Each value in the graph indicates average±S.D. (standard deviation) (n=20). The asterisk (*) indicates a value having a significant difference at 5% significance level.

FIG. 13 is a view showing a change in the leaf size of a wild type (○) and in the leaf size of transgenic *A. thaliana* (●), which has been observed with the course of growing days. Each value in the graph indicates average±S.D. (standard deviation) (n=20). The asterisk (*) indicates a value having a significant difference at 5% significance level.

Each value in the graph indicates average±S.D. (standard deviation) (n=8). The asterisk (*) indicates a value having a significant difference at 5% significance level.

Figure 15:
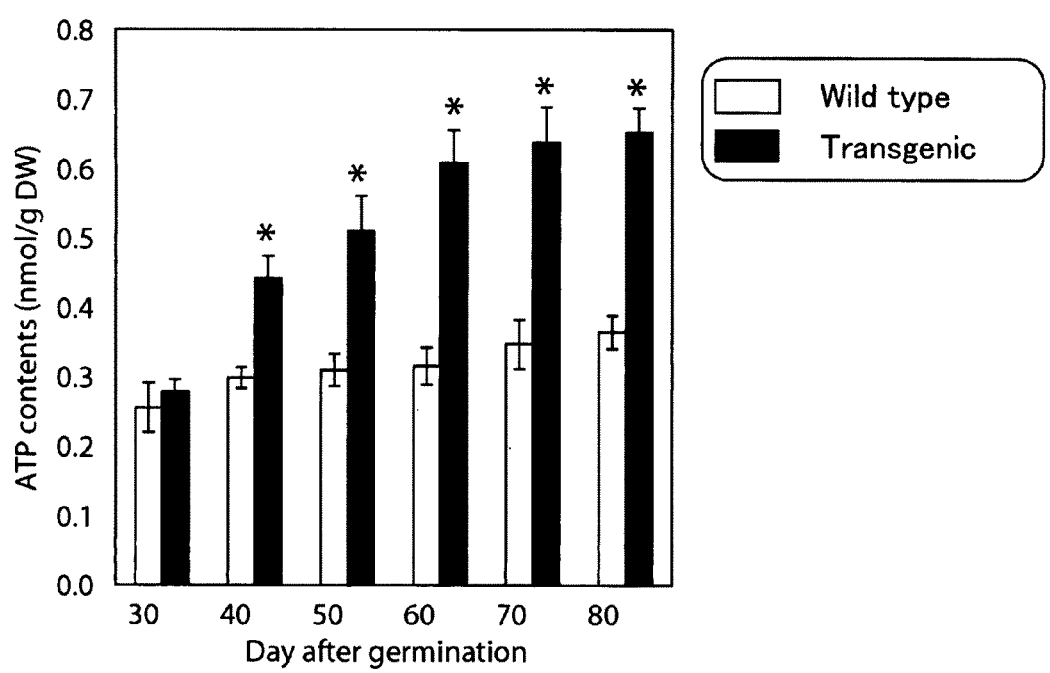

FIG. 15 is a view showing a change in the ATP content of a wild type and in the ATP content of transgenic *A. thaliana*, obtained 3 hours after light irradiation, which has been observed with the course of growing days. Each value in the graph indicates average±S.D. (standard deviation) (n=8). The asterisk (*) indicates a value having a significant difference at 5% significance level.

Figure 16:
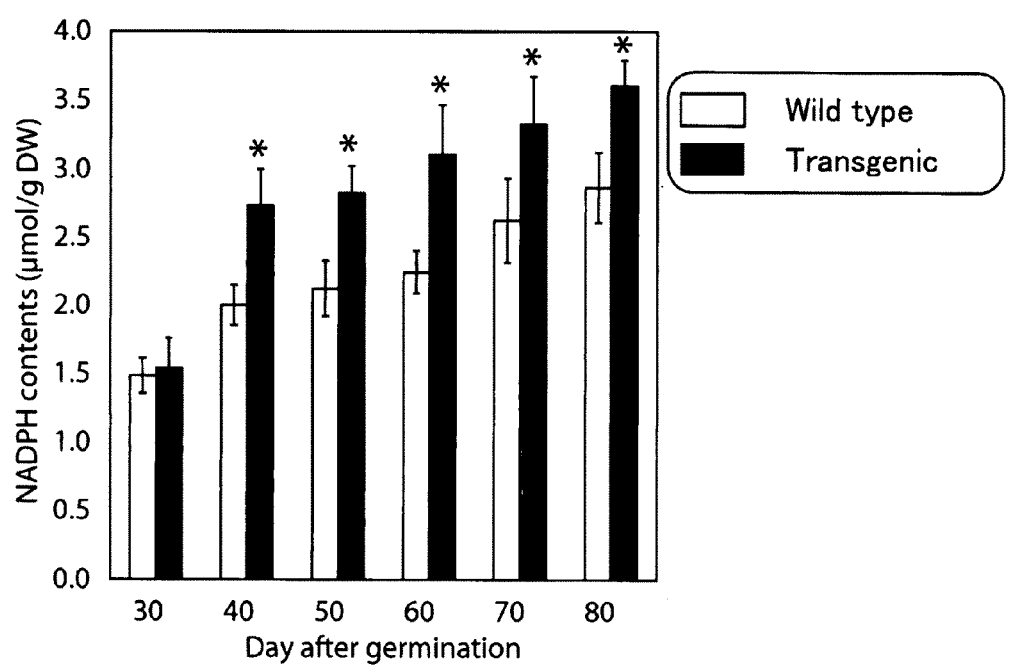

FIG. 16 is a view showing a change in the NADPH content of a wild type and in the NADPH content of transgenic *A. thaliana*, obtained 3 hours after light irradiation, which has been observed with the course of growing days. Each value in the graph indicates average±S.D. (standard deviation) (n=8). The asterisk (*) indicates a value having a significant difference at 5% significance level.

Figure 17:
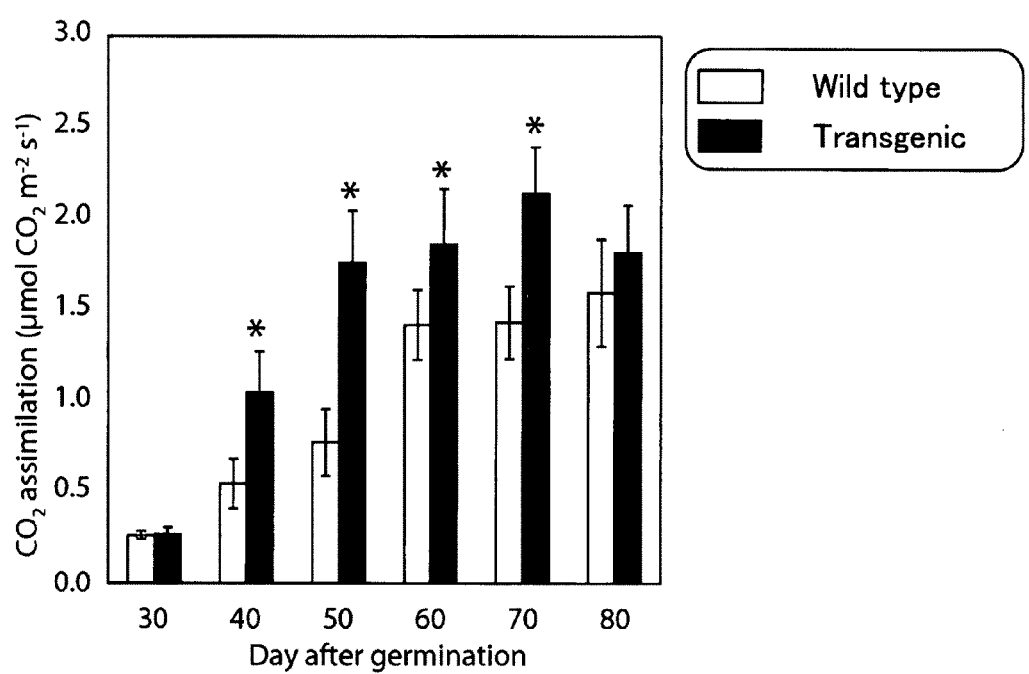

FIG. 17 is a view showing a change in the carbon dioxide-assimilating ability of a wild type and in the carbon dioxide-assimilating ability of transgenic *A. thaliana*, obtained 3 hours after light irradiation, which has been observed with the course of growing days. Each value in the graph indicates average±S.D. (standard deviation) (n=10). The asterisk (*) indicates a value having a significant difference at 5% significance level.

Figure 18:
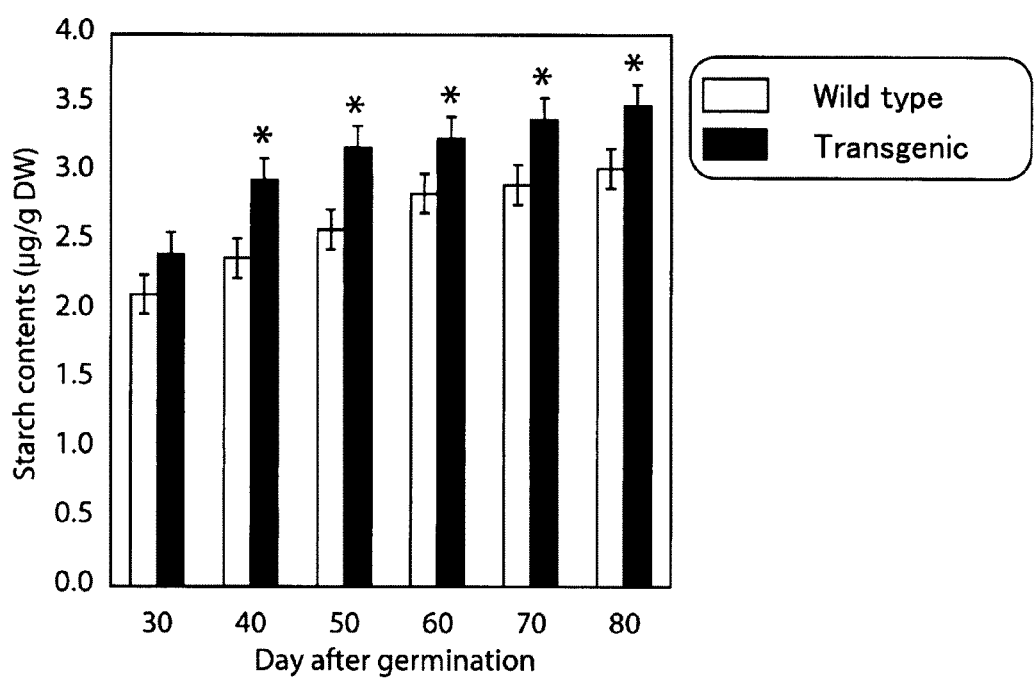

FIG. 18 is a view showing a change in the starch amount contained in a wild type and in the starch amount contained in transgenic *A. thaliana*, obtained 3 hours after light irradiation, which has been observed with the course of growing days. Each value in the graph indicates average±S.D. (standard deviation) (n=10). The asterisk (*) indicates a value having a significant difference at 5% significance level.

Figure 19:
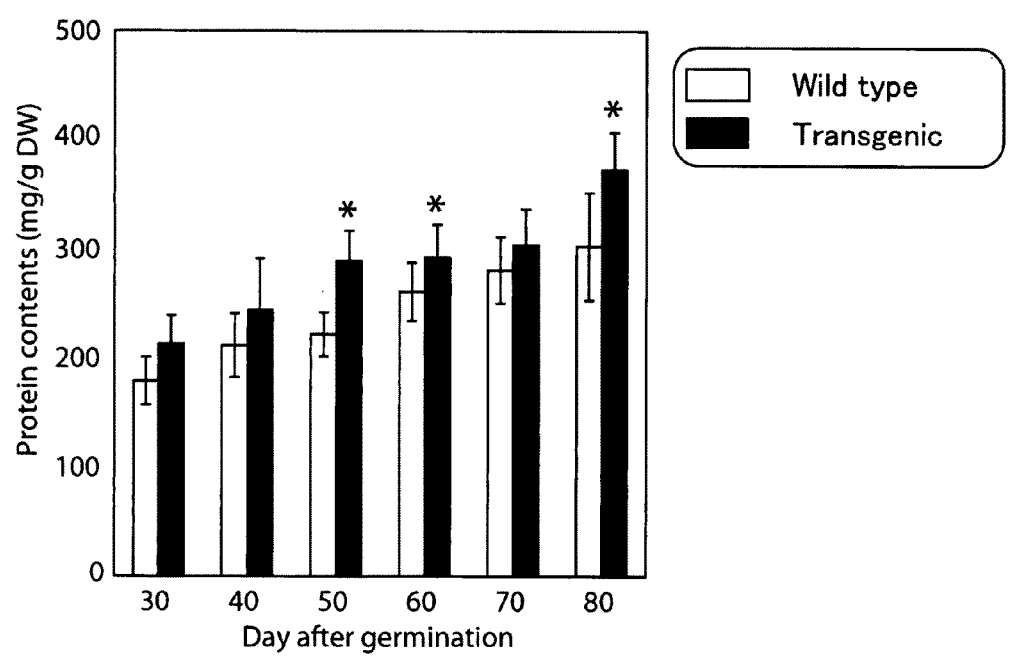

FIG. 19 is a view showing a change in the protein amount contained in a wild type and in the protein amount contained in transgenic *A. thaliana*, obtained 3 hours after light irradiation, which has been observed with the course of growing days. Each value in the graph indicates average±S.D. (standard deviation) (n=8). The asterisk (*) indicates a value having a significant difference at 5% significance level.

The patent or application file contains at least one drawing executed in color. Copies of this patent or patent application publication with color drawing(s) will be provided by the office upon request and payment of the necessary fee.

BEST MODE FOR CARRYING OUT THE INVENTION

The present invention will be described in detail below. However, the following descriptions are not intended to limit the scope of the present invention. Even except for the following examples, changes and modifications may be made without departing from the spirit of the invention.

The present specification includes all of the contents as disclosed in the specification and/or drawings of Japanese Patent Application No. 2005-27012, which is a priority document of the present application. In addition, all prior art publications, patent publications, patent applications, and other patent documents cited herein are incorporated herein by reference in their entirety.

1. Summary of the Present Invention

Figure 1:
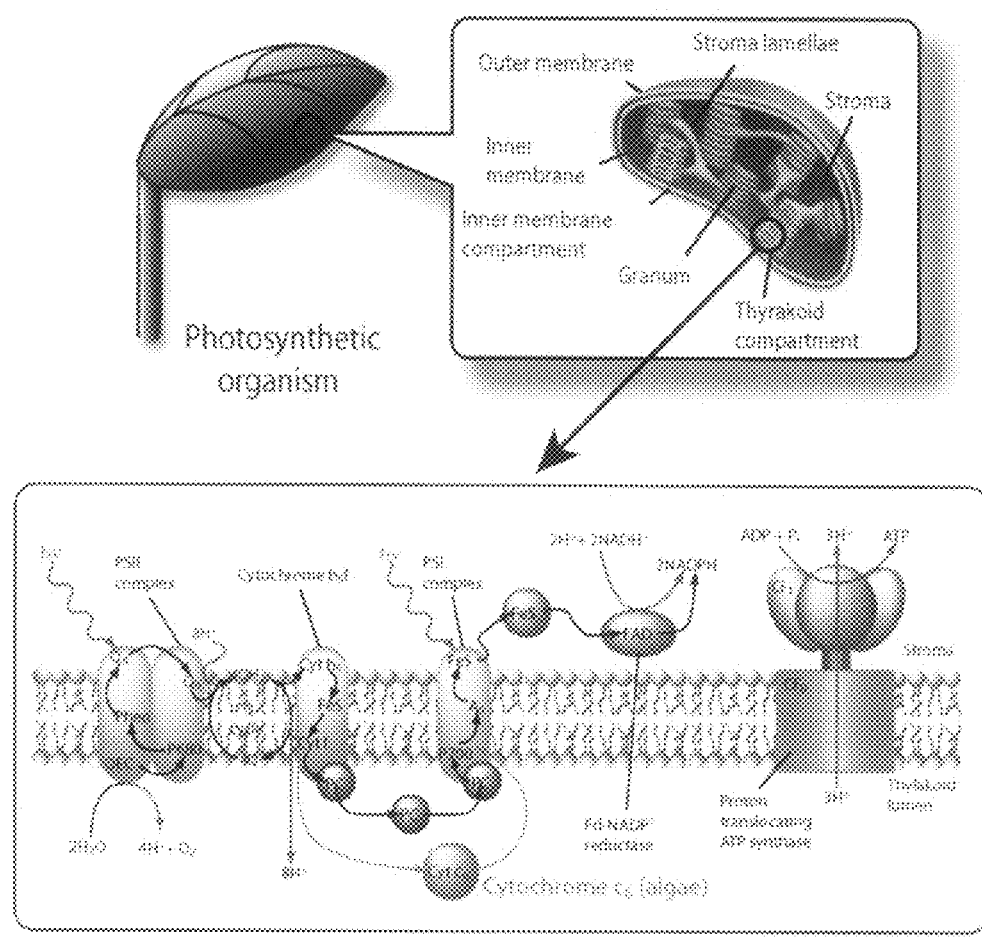
FIG. 1 is a view showing the electron transport system in photosynthesis of a chloroplast thylakoid membrane.
Figure 2:
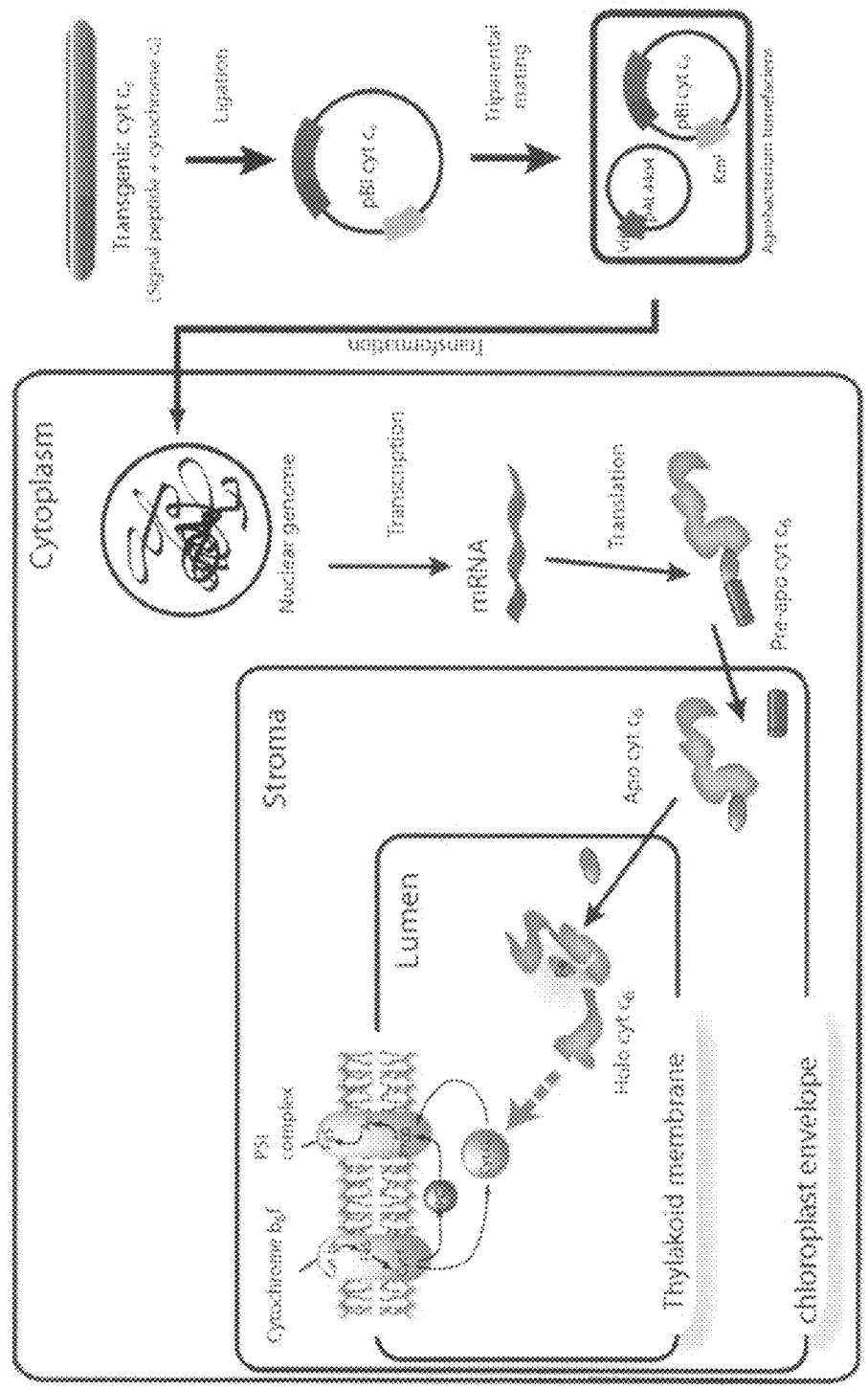
FIG. 2 is a schematic diagram showing introduction of a cytochrome $c_6$ gene into a plant via *Agrobacterium* and the expression manner of cytochrome $c_6$ in the plant in the present invention.

The present invention relates to a method of promoting the growth of a higher plant, which comprises introducing a gene encoding a fused protein consisting of cytochrome $c_6$ and a signal peptide into a higher plant, so as to allow cytochrome $c_6$ acting as an electron carrier in a photosynthetic light reaction to express and function in the thylakoid space of chloroplast of such a higher plant cell (FIG. 2). By the present invention, the synthesis of ATP, NADPH, starch, and protein is promoted in a higher plant cell, and a photosynthetic dark reaction (carbon fixation reaction) of converting carbon dioxide ($CO_2$) to carbohydrate can be thereby promoted. The present invention includes such a method of promoting the synthesis of ATP or carbon fixation in a higher plant, and also includes a method of producing a higher plant, which involves promotion of the growth thereof, promotion of the synthesis of ATP or the like, and promotion of carbon fixation.

In general, in a photosynthetic light reaction (photosynthetic electron-transfer reaction), chlorophyll electrons acquire energy from sunlight, and they move one another through an electron transport chain in the thylakoid space (in the thylakoid membrane). At that time, chlorophyll acquires electrons from water and discharges oxygen ($O_2$). At the same time, with such electron transfer reaction, $H^+$ is pumped out through the thylakoid membrane, and ATP is synthesized in the stroma of chloroplast due to the thus generated proton motive force. Thereafter, at the final stage of a series of reactions, $NADP^+$ accepts high energy electrons (as well as $H^+$), so that NADPH can be synthesized.

In contrast, in a photosynthetic dark reaction (carbon fixation reaction), ATP and NADPH, which have been synthesized by a photosynthetic light reaction, function as an energy source and a reducing power, respectively. As a result, $CO_2$ is converted to carbohydrate in chloroplast stroma and cytoplast. By this carbon fixation reaction, sucrose is synthesized in plant leaves and the like. Sucrose is transported to other tissues, and it is used as a synthetic material for various organic molecules, and in particular, it is used as an energy source for the growth of the plant itself.

Figure 3:
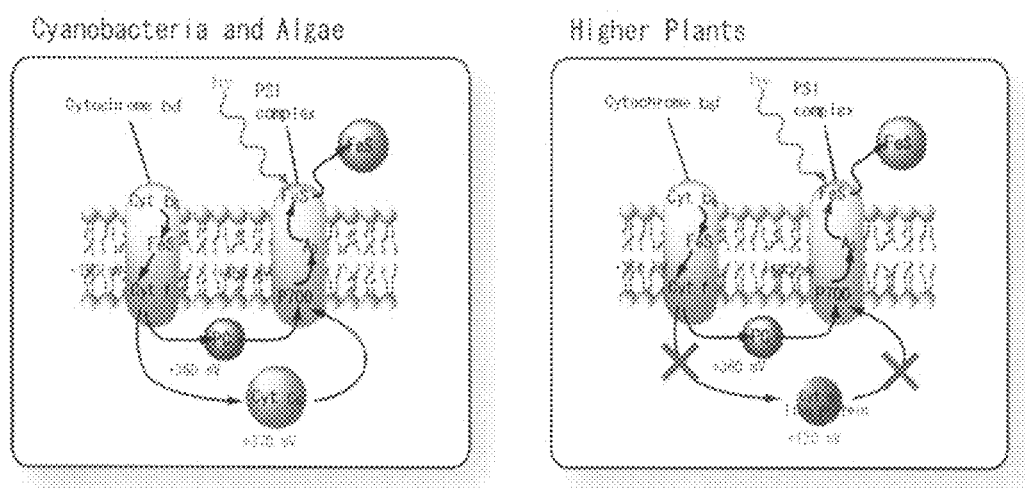
FIG. 3 is a view showing a difference in the electron transfer system between cyanobacteria and algae, and higher plants.

In general, an electron carrier in a photosynthetic light reaction in a higher plant (an electron carrier protein) is considered to be plastocyanin (PC). However, it has been known that cytochrome $c_6$ acting as an electron carrier in algae is superior to plastocyanin (PC) in terms of electron-transferring ability (high oxidation-reduction potential) (FIG. 3). Thus, various attempts have previously been made to allow such cytochrome $c_6$ to express and function in a higher plant, so as to promote a photosynthetic light reaction and a photosynthetic dark reaction. However, as a matter of fact, it has been extremely difficult to carry out such attempts successfully. In fact, there have been no successful examples to date.

In order that a protein that has been allowed to express in a cell of a higher plant based on the genome information thereof exhibits a function as an electron carrier in a photosynthetic light reaction, it is essential for the protein to exist in the thylakoid space thereof. In order that the protein exists in the thylakoid space, in general, it must pass through two types of membranes, a "chloroplast envelope" and a "thylakoid membrane." This point has been considered to be a main cause for extreme difficulty in expression of the function of cytochrome $c_6$ in a higher plant. Hence, when a cytochrome $c_6$ gene has been introduced into the genome of a higher plant via genetic recombination, the present inventor had previously constructed a signal sequence-added gene, such that the cytochrome $c_6$ protein could be expressed in the form of a fused protein obtained by adding a specific signal peptide (a signal peptide having a specific length or a specific amino acid sequence) to the above cytochrome $c_6$ protein. Thereafter, the inventor has introduced the gene into the higher plant. As a result, the presence of the cytochrome $c_6$ protein (without the signal peptide) was observed in the thylakoid space of a plant body produced by the above gene introduction. Thus, it was demonstrated that the expressed fused protein is able to pass through the aforementioned two types of membranes due to the action of the signal peptide thereof, thereby completing the present invention.

(1) Studies Regarding PYC6 Gene Introduction System

To date, it has been known that the oxidation-reduction potential of PYC6 is high. In addition, the genetic sequence of PYC6 has been clarified. In the present invention, the PYC6 gene was first ligated to a binary vector, so as to prepare *Agrobacterium* used in transformation. *Arabidopsis thaliana* was disseminated and was then subjected to a low-temperature treatment. Thereafter, it was allowed to grown under long day conditions. At the stage of formation of flower buds, *Arabidopsis thaliana* was transformed by infiltration under reduced pressure. Subsequently, in order to analyze gene introduction and expression in the obtained transformant, using genomic DNA and RNA extracted from the plant body as templates, PCR and RT-PCR were carried out, respectively. As a result, amplification of the PYC6 gene was observed, and it was confirmed using a DNA sequencer that the nucleotide sequence thereof is the same as that of the PYC6 gene. Subsequently, in order to confirm expression of the PYC6 gene observed in the transformant as a protein, a chloroplast protein fraction was extracted from the plant body, and it was then electrophoresed, followed by performing Western blotting. As a result, expression of the PYC6 protein was confirmed. In addition, the N-terminal amino acid sequence of the PYC6 protein in the obtained transformant was analyzed. As a result, it was found that the obtained N-terminal amino acid sequence was identical to the amino acid sequence of the introduced PYC6 (PIR accession No. JC5849). From these results, it was found that cyt $c_6$ (PYC6) derived from algae was successfully allowed to express in *A. thaliana* that was a higher plant.

(2) Influence of PYC6 Introduction Upon Plant Body

The growth of a PYC6-introduced plant was observed. As a result, as shown in the examples as given later, the size of a leaf thereof was approximately 1.2 to 1.3 times greater than that of a wild type (WT), and the height thereof was approximately 1.5 times greater than that of the wild type (WT). At the initial growth stage, the PYC6-introduced plant had a growth rate that was higher than that of WT. Moreover, as a result of the measurement of the chlorophyll amount contained in the PYC6-introduced plant, it was found that the chlorophyll amount contained in the PYC6-introduced plant was approximately 1.1 to 1.2 times larger than that of WT. It is considered that such a phenomenon occurred in the plant body as a result of the PYC6 introduction was brought on as a result of activation of the entire photosynthetic reaction using an energetic substance as a final product of a light reaction. Thus, the amount of ATP contained in the PYC6-introduced plant was measured by the luciferin-luciferase method. As a result, it was found that the ATP amount contained in the PYC6-introduced plant was approximately 1.7 times larger than that of WT. It was considered that this was because electron transfer in a light reaction was activated by *P. yezoensis* cyt $c_6$ that functioned as a novel electron carrier, as well as plastocyanin that functioned in *A. thaliana*, and the amount of ATP as a final product was thereby increased, and the growth of the plant as a whole was also thereby activated.

When the above fused protein passes through the aforementioned two types of membranes, a part of a signal peptide is used when the protein passes through the first membrane (chloroplast envelope), and the remaining part is used when it passes through the second membrane (thylakoid membrane). Each of the two parts was dissociated from the protein after use, and finally, the above protein is transferred into the thylakoid space in the form of not having such a signal peptide. It is considered that the thus transferred PYC6 protein binds to heme (heme c) in the thylakoid space, followed by folding, so that it becomes cytochrome $c_6$ that is able to function as an electron carrier.

2. Method of Producing Novel Higher Plant

As described above, the production method of the present invention is a method of producing a novel higher plant having cytochrome $c_6$ in the thylakoid space of chloroplast, which is characterized in that it comprises introducing a gene encoding a fused protein formed by adding a signal peptide consisting of 50 to 80 amino acid residues to a cytochrome $c_6$ protein into the genome of a higher plant.

(1) Higher Plant to be Produced

The type of a higher plant that can be used in the production method of the present invention, namely, the type of a higher plant that can be transformed such that it has cytochrome $c_6$ in the thylakoid space of chloroplast, is not limited. For example, the following plants can be used.

The plant used in the present invention includes all of a plant body as a whole, a plant organ (for example, a leaf, a petal, a pedicle, a root, a seed, etc.), a plant tissue (for example, epidermis, phloem, parenchyma, xylem, vascular bundle, palisade tissue, spongy tissue, etc.), and a cultured plant cell (including cultured tissues such as callus). Plants used in transformation include C3, C4 and CAM plants, and all of their intermediate plants. Examples of such a plant include plants belonging to Brassicaceae, Solanaceae, Gramineae, Leguminosae, Chenopodiaceae, Rosaceae, Asteraceae, Liliaceae, Caryophyllaceae, Cucurbitaceae, Convolvulaceae, Amaranthaceae, Bromeliaceae, Cactaceae, and Aloeaceae (including fruits, vegetables, flowers and ornamental plants, and the like) (see below). However, examples are not limited thereto.

[C3 Plants]

Brassicaceae: *Arabidopsis thaliana, Raphanus*, etc.
Solanaceae: *Nicotiana tabacum, Solanum*, etc.
Gramineae: *Oryza sativa, Zea mays, Triticun*, etc.
Leguminosae: *Glycine max, Pisum*, etc.
Chenopodiaceae: *Spinacia*, etc.
Rosaceae: *Prunus, Rosa*, etc.
Asteraceae: *Erigeron, Taraxacun*, etc.
Cucurbitaceae: *Cucurdida, Cucumis*, etc.
Convolvulaceae: *Ipomea*, etc.
Orchidaceae: *Poneorchis*, etc.

[C4 Plants]

Gramineae: *Zea mays, Saccharum officinarum, Setaria itarica*, etc.
Amaranthaceae: Amaranthaceae, etc.

[CAM Plants]

Bromeliaceae: *Ananas comosus*, etc.
Cactaceae: *Lophosphora difusa, Opuntia* spp., etc.
Aloeaceae: *Aloe arborescens, Aloe vera*, etc.

[C3-C4 Intermediate Plants]

Aizoaceae: *Mollugo verticillata*, etc.
Gramineae: *Panicum milioides*, etc.

Among others, as an effect of the production method of the present invention, if taking into consideration the achievement of a plant having a high growth-promoting effect, highly marketable plants are advantageous for the present invention. Specifically, preferred examples of such a highly marketable plant include foliage plants (spinach, cabbage, etc.), flower plants (rose, phalaenopsis, etc.), pedicle plants (potato, lotus root, etc.), root plants (burdock, Japanese radish, etc.), grains (rice, wheat, etc.), fruits (pineapple, grape, etc.), ornamental plants (Pinus, maple, etc.), and woods (*Cryptomeria japonica, Chamaecyparis obtuse*, etc.).

(2) Fused Protein

It is important for the production method of the present invention to introduce a gene encoding a specific fused protein into the genome of a higher plant, or to use a fused protein formed by adding a signal peptide having a certain length to a cytochrome $c_6$ protein.

It is important that the above fused protein has a signal peptide having a length of 50 to 80 amino acid residues. Thus, the fused protein has a signal peptide having a sufficient length, so that it makes the cytochrome $c_6$ protein to pass through both the chloroplast envelope and the thylakoid membrane. The sequence of such a signal peptide can be determined by gene cloning through higher plants.

In general, the signal peptide in the above fused protein is preferably added to the N-terminus of the cytochrome $c_6$ protein.

In the present invention, the above fused protein is preferably the protein described in the following (a), (b), (c), or (d), for example:
(a) a protein having the amino acid sequence as shown in SEQ ID NO: 6;
(b) a protein, which has an amino acid sequence comprising a deletion, substitution, or addition of one or several amino acids with respect to an amino acid sequence portion corresponding to the above-described signal peptide in the amino acid sequence as shown in SEQ ID NO: 6, and which has ability to pass through the chloroplast envelope and thylakoid membrane of a higher plant;
(c) a protein, which has an amino acid sequence comprising a deletion, substitution, or addition of one or several amino acids with respect to an amino acid sequence portion corresponding to the above-described cytochrome $c_6$ protein in the amino acid sequence as shown in SEQ ID NO: 6, and which has ability to transfer electrons; and
(d) a protein, which has an amino acid sequence comprising a deletion, substitution, or addition of one or several amino acids with respect to each of an amino acid sequence portion corresponding to the above-described signal peptide and an amino acid sequence portion corresponding to the above-described cytochrome $c_6$ protein in the amino acid sequence as shown in SEQ ID NO: 6, and which has ability to pass through the chloroplast envelope and thylakoid membrane of a higher plant and ability to transfer electrons.

As shown in SEQ ID NO: 6, the protein described in (a) above consists of total 157 amino acids, and it is formed by adding a signal peptide sequence consisting of 72 amino acids (SEQ ID NO: 4) to the N-terminal side of a cytochrome $c_6$ protein sequence consisting of 85 amino acids (SEQ ID NO: 2). It may also be a fused protein having the amino acid sequence as shown in SEQ ID NO: 6. However, such a signal peptide is not limited to the above signal peptide having 72 amino acids. The origin of the cytochrome $c_6$ protein is not particularly limited herein, and *Porphyra yezoensis*, blue-green algae, brown algae, Bacillariophyta, Chlorophyceae, and the like can be used. The cytochrome $c_6$ protein used herein is preferably derived from *P. yezoensis*. The amino acid sequence of the cytochrome $c_6$ protein derived from *P. yezoensis* has been known (PIR accession No. JC5849). It can be obtained by database searching.

The type of the protein described in (b) above is not limited, as long as it has an amino acid sequence comprising a deletion, substitution, or addition of one or several amino acids (for example approximately 1 to 10 amino acids, and preferably approximately 1 to 5 amino acids) with respect to the amino acid sequence portion consisting of 72 amino acids (SEQ ID NO: 4) corresponding to the above-described signal peptide in the total amino acid sequence that constitutes the protein described in (a) above, and which has ability to pass through the chloroplast envelope and thylakoid membrane of a higher plant.

It is important for the protein described in (b) above to have ability to pass through the chloroplast envelope and thylakoid membrane of a higher plant, as with the protein described in (a) above. Accordingly, it is preferable that an amino acid sequence portion that is considered to be important for passing through the above chloroplast envelope or thylakoid membrane, such as amino acids from position 53 to position 72, be not mutated or substituted from the amino acid sequence of the protein described in (a) above.

The type of the protein described in (c) above is not limited, as long as it has an amino acid sequence comprising a deletion, substitution, or addition of one or several amino acids (for example approximately 1 to 10 amino acids, and preferably approximately 1 to 5 amino acids) with respect to the amino acid sequence portion consisting of 85 amino acids (SEQ ID NO: 6) corresponding to the above-described cytochrome $c_6$ protein in the total amino acid sequence that constitutes the protein described in (a) above, and which has ability to transfer electrons (in a photosynthetic light reaction).

Herein, the above term "protein having ability to transfer electrons" is used in the present invention to mean a protein having an amino acid sequence portion obtained by eliminating an amino acid sequence portion corresponding to the above-described signal peptide from the total amino acid sequence that constitutes the protein described in (c) above, wherein the above-described protein has electron-transferring ability after it has bound to heme (heme c).

As in the case of the cytochrome $c_6$ protein, it is important for the protein described in (c) above to have electron-transferring ability. Accordingly, it is preferable that an amino acid sequence portion that is considered to be important for functioning as an electron carrier in the photosynthetic light reaction of a higher plant, such as amino acids from position 14 to position 18 and amino acids from position 47 to 60, be not mutated or substituted from the amino acid sequence of the protein described in (a) above.

The type of the protein described in (d) above is not limited, as long as it has an amino acid sequence comprising a deletion, substitution, or addition of one or several amino acids (for example approximately 1 to 10 amino acids, and preferably approximately 1 to 5 amino acids) with respect to the amino acid sequence portion consisting of 72 amino acids corresponding to the above-described signal peptide (SEQ ID NO: 4) and also has an amino acid sequence comprising a deletion, substitution, or addition of one or several amino acids (for example approximately 1 to 10 amino acids, and preferably approximately 1 to 5 amino acids) with respect to the amino acid sequence portion consisting of 85 amino acids corresponding to the above-described cytochrome $c_6$ protein (SEQ ID NO: 2), in the total amino acid sequence that constitutes the protein described in (a) above, and which has ability to pass through the chloroplast envelope and thylakoid membrane of a higher plant and ability to transfer electrons (in a photosynthetic light reaction).

Herein, the above term "protein having ability to transfer electrons" has the same meaning as that in the case of the protein described in (c) above.

It is important for the protein described in (d) above to have ability to pass through the chloroplast envelope and thylakoid membrane of a higher plant as with the protein described in (a) above, and also to have electron-transferring ability as with the cytochrome $c_6$ protein. Accordingly, it is preferable that an amino acid sequence portion that is considered to be important for passing through the above chloroplast envelope or thylakoid membrane, such as amino acids from position 53 to position 72, or an amino acid sequence portion that is considered to be important for functioning as an electron carrier in the photosynthetic light reaction of a higher plant, such as amino acids from position 14 to position 18 and amino acids from position 47 to 60, be not mutated or substituted from the amino acid sequence of the protein described in (a) above.

The presence or absence of the electron-transferring ability of the proteins described in (c) and (d) above, or such electron-transferring ability if the above proteins have such ability, can be confirmed or measured by three-dimensional structure analysis and the measurement of oxidation-reduction potential. It is to be noted that the oxidation-reduction potential of cytochrome $c_6$ is between approximately 350 and 370 mV.

A polynucleotide encoding an amino acid sequence comprising a deletion, insertion, or addition of one or several amino acids with respect to the amino acid sequence as shown in SEQ ID NO: 6 can be prepared according to methods such as site-directed mutagenesis described in "Molecular Cloning, A Laboratory Manual 2nd ed." (Cold Spring Harbor Press (1989)); "Current Protocols in Molecular Biology" (John Wiley & Sons (1987-1997); Kunkel (1985) Proc. Natl. Acad. Sci. USA 82: 488-92; and Kunkel (1988) Method. Enzymol. 85: 2763-6; etc. Such a gene encoding a mutant amino acid sequence, such as an amino acid sequence comprising a deletion, substitution, addition, etc. of amino acids, can be produced by known methods such as the Kunkel method or the Gapped duplex method, using a mutation introduction kit that utilizes site-directed mutagenesis, such as QuikChange™ Site-Directed Mutagenesis Kit (manufactured by Stratagene), GeneTailor™ Site-Directed Mutagenesis System (manufactured by Invitrogen), or TaKaRa Site-Directed Mutagenesis System (Mutan-K, Mutan-Super Express Km, etc.: manufactured by TAKARA BIO INC.).

(3) Gene

In the production method of the present invention, it is important that a gene to be introduced into the genome of a higher plant is a gene encoding the aforementioned fused protein.

In the present invention, the above gene preferably comprises the DNA described in the following (a) or (b), for example. It is to be noted that both the DNAs described in the following (a) and (b) are the structural genes of the aforementioned fused protein (namely, a gene formed by ligating a gene encoding a signal peptide to the structural gene of cytochrome $c_6$ or a protein having electron-transferring ability equivalent to that of the cytochrome $c_6$). A gene comprising such DNAs may consist of only such DNAs. Otherwise, it may comprise such DNAs and other known nucleotide sequences necessary for expression of the structural gene of the above fused protein (a transcriptional promoter, an SD sequence, a Kozak sequence, a terminator, etc.). Thus, the type of a gene comprising such DNAs is not limited. The nucleotide sequence encoding cytochrome $c_6$ has been made public to DNA Data Bank of Japan (DDBJ), and thus it has been known (Accession number: AB40818).

(a) DNA having the nucleotide sequence as shown in SEQ ID NO: 5

(b) DNA, which hybridizes with DNA having a nucleotide sequence complementary to the DNA having the nucleotide sequence as shown in SEQ ID NO: 5 under stringent conditions, and which encodes a protein having ability to pass through the chloroplast envelope and thylakoid membrane of a higher plant and ability to transfer electrons The DNA described in (b) above can be obtained by performing a known hybridization method such as colony hybridization, plaque hybridization, or Southern blotting, using the DNA described in (a) above, DNA having a nucleotide sequence complementary thereto, or a fragment thereof, as a probe, and then utilizing a cDNA library or a genome library. As such a library, a library produced by a known method may be used. Otherwise, a commercially available cDNA library or genome library may also be used. Thus, the type of a library used herein is not limited.

In addition, both the nucleotide sequence encoding the signal peptide portion (SEQ ID NO: 3) and the nucleotide sequence encoding cytochrome $c_6$ (SEQ ID NO: 1), or either the nucleotide sequence as shown in SEQ ID NO: 3 or the nucleotide sequence as shown in SEQ ID NO: 1, may comprise a mutation.

For detailed procedures of hybridization methods, please refer to Molecular Cloning, A Laboratory Manual 2nd ed. (Cold Spring Harbor Laboratory Press (1989)) or other publications, as appropriate.

The term "stringent conditions" regarding hybridization methods is used to mean conditions that are applied during washing after hybridization. Such stringent conditions are that the salt concentration in a buffer is between 15 and 750 mM, and preferably between 15 and 150 mM, and that the temperature is between 25° C. and 65° C., and preferably between 45° C. and 55° C. Specific examples are conditions consisting of 50 mM and 50° C. Moreover, in addition to conditions such as a salt concentration and temperature, taking into consideration various conditions such as a probe concentration, a probe length, or a reaction time, conditions necessary for obtaining the DNA described in (b) above can be determined, as appropriate.

Furthermore, the DNA described in (b) above can be obtained by producing a probe using a suitable fragment according to a method known to persons skilled in the art, then performing a known hybridization method such as colony hybridization, plaque hybridization, or Southern blotting, using the above probe, and then utilizing a cDNA library and a genome library. Examples of stringent conditions applied in the above hybridization include 1×SSC to 2×SSC, 0.1% to 0.5% SDS, and 30° C. to 80° C. More specifically, after completion of pre-hybridization at 60° C. to 68° C. for 30 minutes or more, a probe is added to the reaction product, and the mixture is retained at 68° C. for 1 hour or more, so as to form a hybrid. Thereafter, the hybrid is washed with 2×SSC in 0.1% SDS once or twice at room temperature for 5 to 15 minutes.

DNA used in hybridization has a nucleotide sequence showing homology of at least 70%, more preferably 80% or more, further more preferably 90% or more, and particularly preferably 95% or more, with the nucleotide sequence of the DNA described in (a) above.

It is important that the DNA described in (b) above encodes a protein having ability to pass through the chloroplast envelope and thylakoid membrane of a higher plant and ability to transfer electrons. Accordingly, taking into consideration the amino acid sequence obtained after translation, the above DNA preferably has a nucleotide sequence, regarding which an amino acid sequence portion that is considered to be important for passing through the above chloroplast envelope or thylakoid membrane, such as amino acids from position 53 to position 72, or an amino acid sequence portion that is considered to be important for functioning as an electron carrier in the photosynthetic light reaction of a higher plant, such as amino acids from position 14 to position 18 and amino acids from position 47 to 60, be not mutated or substituted from the amino acid sequence of the protein described in (a) above.

Preferred examples of the DNA described in (b) above include: DNA that has been mutated, such that the amino acid obtained by substituting the nucleotide at position 103 "T (thymine)" with "A (adenine)" of the DNA described in (a) above, followed by translation, is changed from "Ser (serine)" to "Thr (threonine);" DNA that has been mutated, such that the translated amino acid is not changed although the nucleotide at position 216 "C (cytosine)" has been substituted with "T (thymine);" and DNA that has been mutated by the combined use of such nucleotide substitutions.

In the present invention, the above gene is allowed to express in a higher plant. Thus, it is necessary that the above gene comprise DNA wherein codons corresponding to amino acids are those commonly used in plants after transcription (preferably, frequently-used codons).

(4) Gene Introduction Method

The type of a method of producing a novel higher plant (a transgenic higher plant) by introducing a gene encoding the aforementioned fused protein (a gene of interest) into the genome of a higher plant without changing other traits is not limited. Known genetic recombination techniques such as the Agrobacterium method, the electroporation method, or the particle gun method, can be arbitrarily adopted. For example, a vacuum infiltration method using bacteria of genus Agrobacterium (crown gall bacteria), into which a binary vector comprising a gene of interest has been introduced, is preferably applied, but examples are not limited thereto. The details will be described below.

(i) Recombinant Vector

The type of a recombinant vector comprising a gene encoding the aforementioned fused protein is not limited. A vector that can be used as the aforementioned binary vector is preferable. Specifically, a recombinant vector constructed by inserting a gene of interest to be incorporated into plant genome (instead of a GUS gene) into a T-DNA region of a vector having the T-DNA region that is cut out by the action of a Vir region gene, is preferable. Preferred examples of a vector having the above T-DNA region include a pBI121 vector (manufactured by Clontech; the vector having a kanamycin resistance gene as a selective marker and comprising a GUS gene downstream of a 35S promoter), and a pBI101 vector (manufactured by Clontech; the vector having a kanamycin resistance gene as a selective marker and comprising a GUS gene).

In addition, a recombinant vector that is constructed by inserting a gene of interest into a known expression vector suitable for a host cell is also included in the recombinant vector of the present invention. However, this vector cannot be used for the vacuum infiltration method. As necessary, a transcriptional promoter, an SD sequence (in a case where a host is a prokaryocyte), or a Kozak sequence (in a case where a host is a eukaryote) may be added upstream of the above gene by PCR or the like. In addition, a terminator may be added downstream thereof by PCR or the like. Various elements necessary for expression of a fused protein, such as the aforementioned transcriptional promoter, may be comprised in a gene of interest. If such elements are originally comprised in an expression vector, they may also be used. Thus, the origins of such necessary elements are not limited. Such a recombinant vector can be used in mass production of the aforementioned fused protein, etc.

In order to produce various types of recombinant vectors, known genetic recombination techniques and conditions, such as a method using restriction enzymes or a method using topoisomerase, can be adopted and used, as appropriate.

(ii) Transformant Produced by Introduction of Recombinant Vector

The type of a host, into which a recombinant vector is introduced, is not limited. When the vacuum infiltration method is carried out at the final stage, bacteria of genus Agrobacterium (Agrobacterium tumefaciens, etc.) are used as a host, into which a binary vector is introduced. When such bacteria of genus Agrobacterium are used, a previously-transformed cell mass (a transformant of bacteria of genus Agrobacterium), which is produced by destroying or eliminating a cancer gene in the T-DNA region on a Ti plasmid, originally owned by the above bacteria, is generally used. In another case, when an expression vector is introduced as a recombinant vector, known hosts such as Escherichia coli, Bacillus subtilis, yeast, mold, or various types of animal cells including human cells or mouse cells, can be used.

The type of a method of transforming a host is not limited. While taking into consideration the combination of a host and a recombinant vector, a suitable method can be appropriately selected from known methods, and it can be applied. Preferred examples of such a transformation method include electroporation, lipofection, the heat shock method, the PEG method, the calcium phosphate method, and the DEAE dextran method.

With respect to the obtained transformant, the actually used host may be either identical to or different from a host with the codon type of an EBNA1 mutant gene contained in the recombinant vector. Thus, it is not limited.

(iii) Transformation of Higher Plant and Transgenic Higher Plant

The type of a method of introducing a gene of interest into the genome of a higher plant to produce a transgenic higher plant is not limited. The aforementioned vacuum infiltration method is preferable. In addition, it is preferable that a plant body to be transformed be in the form of an adult plant or a callus.

Specifically, a method of transforming a higher plant via the vacuum infiltration method comprises: (a) infecting the lamina of a higher plant with transgenic bacteria (a transformant of bacteria of genus Agrobacterium) that contain a recombinant vector (a binary vector), into which a gene encoding the aforementioned fused protein has been inserted; (b) culturing the lamina in a selective medium that contains antibiotics such as kanamycin; and (c) forming an adventitious bud callus and then allowing it to grow, so as to obtain a transgenic higher plant. When such a vacuum infiltration method is applied, all means and treatment conditions applied in each treating step are not limited, and they may be appropriately selected from a known range.

A gene encoding the aforementioned fused protein has been introduced into the genome of the thus obtained transgenic higher plant. A fused protein allowed to express based on the above gene has the aforementioned signal peptide, and it has ability to pass through the chloroplast envelope and thylakoid membrane of a plant cell. Accordingly, the obtained transgenic higher plant has cytochrome $c_6$ (preferably cytochrome $c_6$ acting as an electron carrier in a photosynthetic light reaction) in the thylakoid space thereof.

It is considered that not only plastocyanin (PC) but also cytochrome $c_6$ functions as an electron carrier in a photosynthetic light reaction in the obtained transgenic higher plant, and promotion of the growth of the plant is thereby effectively achieved. However, the size (height, root length, leaf size, etc.) of the adult body of such a transgenic higher plant is not limited. The size of such a transgenic higher plant is for example 1.1 times or more, preferably 1.2 times or more, and more preferably 1.5 times or more (for example, approximately 1.9 times) greater than that of a wild-type higher plant.

In addition, such a transgenic higher plant has the effect of increasing the numbers of various types of molecules in each cell, as well as the effect of promoting the growth thereof. For example, the quantities of chlorophyll molecules are not limited, but they are for example 1.1 times or more, preferably 1.2 times or more, and more preferably 1.5 times or more (for example, approximately 1.6 times) larger than those of a wild-type higher plant. Thus, the transgenic higher plant has photosynthetic ability that has been further improved.

Moreover, since the obtained transgenic higher plant has a photosynthetic efficiency that has been improved, the synthetic amount of ATP as a product thereof is for example 1.1 times or more, preferably 1.2 times or more, and more preferably 1.5 times or more (for example, approximately 1.7 times) larger than that of a wild-type higher plant, but such a synthetic amount is not limited thereto. Likewise, the synthetic amount of NADPH is for example 1.1 times or more, preferably 1.2 times or more, and more preferably 1.5 times or more (for example, approximately 1.7 times) larger than that of a wild-type higher plant, but such a synthetic amount is not limited thereto.

Furthermore, in the obtained transgenic higher plant, as the synthetic amount of ATP and that of NADPH increase, the efficiency of a photosynthetic dark reaction, in which such ATP and NADPH function as an energy source or a reduction power, is also improved. For example, the transgenic higher plant has carbon fixation ability to convert carbon dioxide ($CO_2$) to carbohydrate that is for example 1.1 times or more, preferably 1.2 times or more, and more preferably 1.4 times or more greater than that of a wild-type higher plant.

Still further, as a result that the efficiency of a photosynthetic light reaction or a photosynthetic dark reaction has been promoted in the obtained transgenic higher plant, the efficiency of protein synthesis has also been improved. For example, the transgenic higher plant has a protein content that is for example 1.1 times or more, preferably 1.2 times or more, and more preferably 1.5 times or more larger than that of a wild-type higher plant.

Still further, sulfuric acid and nitric acid metabolism, the synthesis of various types of amino acids, the synthetic amount of lipid, and an increase in pigment and flowers, etc. can also be anticipated.

The obtained transgenic higher plant has preferably at least one of, more preferably two or more of, and further more preferably all of, various types of the aforementioned effects.

3. Method of Promoting Growth of Higher Plant Method of Promoting Synthesis of ATP, NADPH, Starch and Protein, and Method of Promoting Carbon Fixation As described above, the obtained transgenic higher plant has (i) the effect of promoting the growth thereof, (ii) the effect of promoting the synthesis of ATP, NADPH, a starch, and a protein, and (iii) the effect of promoting carbon fixation. Accordingly, the present invention also includes a method of promoting the growth of a higher plant, a method of promoting the synthesis of at least one selected from the group consisting of ATP, NADPH, a starch and a protein of a higher plant, and a method of promoting the carbon fixation of a higher plant.

Specifically, these methods are characterized in that they comprise: introducing into the genome of a higher plant a gene encoding a fused protein formed by adding a signal peptide consisting of 50 to 80 amino acid residues to a cytochrome $c_6$ protein, so as to allow it to express therein; and allowing cytochrome $c_6$ to exist in the thylakoid space of chloroplast. In these methods, with respect to a fused protein, a gene encoding the above protein, a method of introducing the above gene into a higher plant genome, various effects obtained from the obtained transgenic higher plant, and the like, the aforementioned descriptions, examples, and others, which are given regarding the method of producing a higher plant of the present invention, can also be applied.

The present invention will be more specifically described in the following examples. However, these examples are not intended to limit the scope of the present invention.

EXAMPLE 1

Construction of Cytochrome $c_6$ Gene to be Introduced and Expression Vector Used for Plants (1) Preparation of *Porphyra yezoensis*-Derived Cytochrome $c_6$ Mature Protein Region Gene In the present example, a *P. yezoensis*-derived cytochrome $c_6$ gene was acquired by cloning, and it was then ligated to a vector, so as to prepare a plasmid. Using this plasmid as a template, a *P. yezoensis*-derived cytochrome $c_6$ mature protein region gene that was DNA of interest in this example was amplified. Thereafter, electrophoresis was carried out. A gene of interest was extracted by gel extraction, and it was then digested with restriction enzymes (SacI and PstI), so as to prepare a gene.

The reaction solution with the following composition was prepared in a 0.5-ml assist PCR tube.

| | |
|---|---|
| Template (plasmid DNA (overall length of cytochrome $c_6$)) | 1.0 µl |
| Primer (1) (10 pmol/µl) | 1.0 µl |
| Primer (2) (10 pmol/µl) | 1.0 µl |
| 10 x Ex Taq buffer ($Mg^{2+}$ plus) ($Mg^{2+}$ concentration: 20 mM) | 2.5 µl |
| dNTP Mixture (2.5 mM each) | 2.0 µl |
| DMSO | 1.25 µl |
| Distilled water | 16.1 µl |
| TaKaRa Ex Taq (5 U/µl) | 0.15 µl |
| Total volume | 25.0 µl |

Primer (1): PYC6-C-term SacI (10 pmol/µl) (30 mer, GC-Cont.: 43.3%)
5'-GGA GCT CTT ACC AAC CTT TTT CAG ATT GAG-3' (SEQ ID NO: 7)
Primer (2): Cyt-SD (10 pmol/µl) (29 mer, GC-Cont.: 48.2%)
5'-CCG CGG AGA CGT TAA ATT GAA GAA GAA GC-3' (SEQ ID NO: 8)

15 µl of mineral oil was laminated on the above reaction solution. Thereafter, a reaction was carried out using PTC-100™ Programmable Thermal Controller. A reaction consisting of 94° C.-48 seconds, 62° C.-48 seconds, and 72° C.-1 minute 24 seconds was defined as 1 cycle. 31 cycles of reactions were carried out.

After completion of the reaction, confirmation was carried out by 2% (w/v) agarose gel electrophoresis. 4 µl of a gel loading buffer was added to 20 µl of the obtained PCR product, and the obtained mixture was used as an electrophoretic sample. Electrophoresis was carried out at 100 V for 30 minutes using an electrophoresis buffer (1×TBE). After completion of the electrophoresis, the gel was stained with 0.1 mg/ml ethidium bromide for 7 minutes, and it was then decolorized with extra pure water for 10 minutes. The decolorized gel was placed on a UV transilluminator, and it was then photographed with a nonautomatic hooded instant camera.

A band that was considered to be DNA of interest was cut out of 2% (w/v) agarose gel, and it was then minced as finely as possible. The gel was placed in Amicon Ultra free (registered trade mark) DA, and it was then centrifuged at 7,300 rpm at 4° C. for 10 minutes. After completion of the centrifugation, Ultra free MC (a column portion on the upper side) was removed, and to the eluted solution, an equal amount of TE-saturated Phenol was added. Thereafter, the mixture was fully stirred using a vortex, followed by centrifugation at 14,000 rpm at 4° C. for 10 minutes. The water layer was transferred into a new 1.5 ml microcentrifuge tube, and 1/20 vol. of 3 M NaOAc (pH 5.2) and 2 vol. of 99.5% ethanol were then added thereto. After the mixture had been fully stirred, it was left at −20° C. for 30 minutes. Thereafter, the resultant was centrifuged at 14,000 rpm at 4° C. for 10 minutes, and the supernatant was then discarded. 500 µl of 75% ethanol was added to the precipitate, and the precipitate was then fully washed. The resultant was further centrifuged at 14,000 rpm at 4° C. for 5 minutes, and the supernatant was then discarded. The precipitate was air-dried to a certain extent, and it was then dissolved in 50 µl of TE.

Subsequently, a sample having the following composition was prepared in a 1.5 ml microcentrifuge tube. The sample was then incubated at 37° C. for 120 minutes, so that it was digested with the restriction enzyme SacI.

| Sample obtained after gel extraction | 5.0 µl |
| --- | --- |
| 10 × L Buffer | 2.0 µl |
| SacI | 0.5 µl |
| Distilled water | 12.5 µl |
| Total volume | 20.0 µl |

To a sample solution obtained after incubation, an equal amount of TE-saturated Phenol was added. Thereafter, the mixture was fully stirred using a vortex, followed by centrifugation at 14,000 rpm at 4° C. for 10 minutes. The water layer was transferred into a new 1.5 ml microcentrifuge tube, and 1/20 vol. of 3 M NaOAc (pH 5.2) and 2 vol. of 99.5% ethanol were then added thereto. After the mixture had been fully stirred, it was left at −20° C. for 30 minutes. Thereafter, the resultant was centrifuged at 14,000 rpm at 4° C. for 10 minutes, and the supernatant was then discarded. 500 µl of 75% ethanol was added to the precipitate, and the precipitate was then fully washed. The resultant was further centrifuged at 14,000 rpm at 4° C. for 5 minutes, and the supernatant was then discarded. The precipitate was air-dried to a certain extent, and it was then dissolved in 20 µl of TE.

Subsequently, a sample having the following composition was prepared in a 1.5 ml microcentrifuge tube. The sample was then incubated at 37° C. for 120 minutes, so that it was digested with the restriction enzyme PstI.

| Sample after digestion with restriction enzyme | 5.0 µl |
| --- | --- |
| 10 × H Buffer | 2.0 µl |
| PstI | 0.5 µl |
| Distilled water | 12.5 µl |
| Total volume | 20.0 µl |

After completion of the reaction, confirmation was carried out by 2% (w/v) agarose gel electrophoresis. 4 µl of a gel loading buffer was added to 20 µl of the obtained PCR product, and the obtained mixture was used as an electrophoretic sample. Electrophoresis was carried out at 100 V for 30 minutes using an electrophoresis buffer (1×TBE). After completion of the electrophoresis, the gel was stained with 0.1 mg/ml ethidium bromide for 7 minutes, and it was then decolorized with extra pure water for 10 minutes. The decolorized gel was placed on a UV transilluminator, and it was then photographed with a nonautomatic hooded instant camera. Thereafter, a band that was considered to be DNA of interest was cut out of 2% (w/v) agarose gel, and it was then minced as finely as possible. The gel was placed in Amicon Ultra free (registered trade mark) DA, and it was then centrifuged at 7,300 rpm at 4° C. for 10 minutes. After completion of the centrifugation, Ultra free MC (a column portion on the upper side) was removed, and to the eluted solution, an equal amount of TE-saturated Phenol was added. Thereafter, the mixture was fully stirred using a vortex, followed by centrifugation at 14,000 rpm at 4° C. for 10 minutes. The water layer was transferred into a new 1.5 ml microcentrifuge tube, and 1/20 vol. of 3 M NaOAc (pH 5.2) and 2 vol. of 99.5% ethanol were then added thereto. After the mixture had been fully stirred, it was left at −20° C. for 30 minutes. Thereafter, the resultant was centrifuged at 14,000 rpm at 4° C. for 10 minutes, and the supernatant was then discarded. 500 µl of 75% ethanol was added to the precipitate, and the precipitate was then fully washed. The resultant was further centrifuged at 14,000 rpm at 4° C. for 5 minutes, and the supernatant was then discarded. The precipitate was air-dried to a certain extent, and it was then dissolved in 20 µl of TE.

The following results were obtained.

Figure 4:
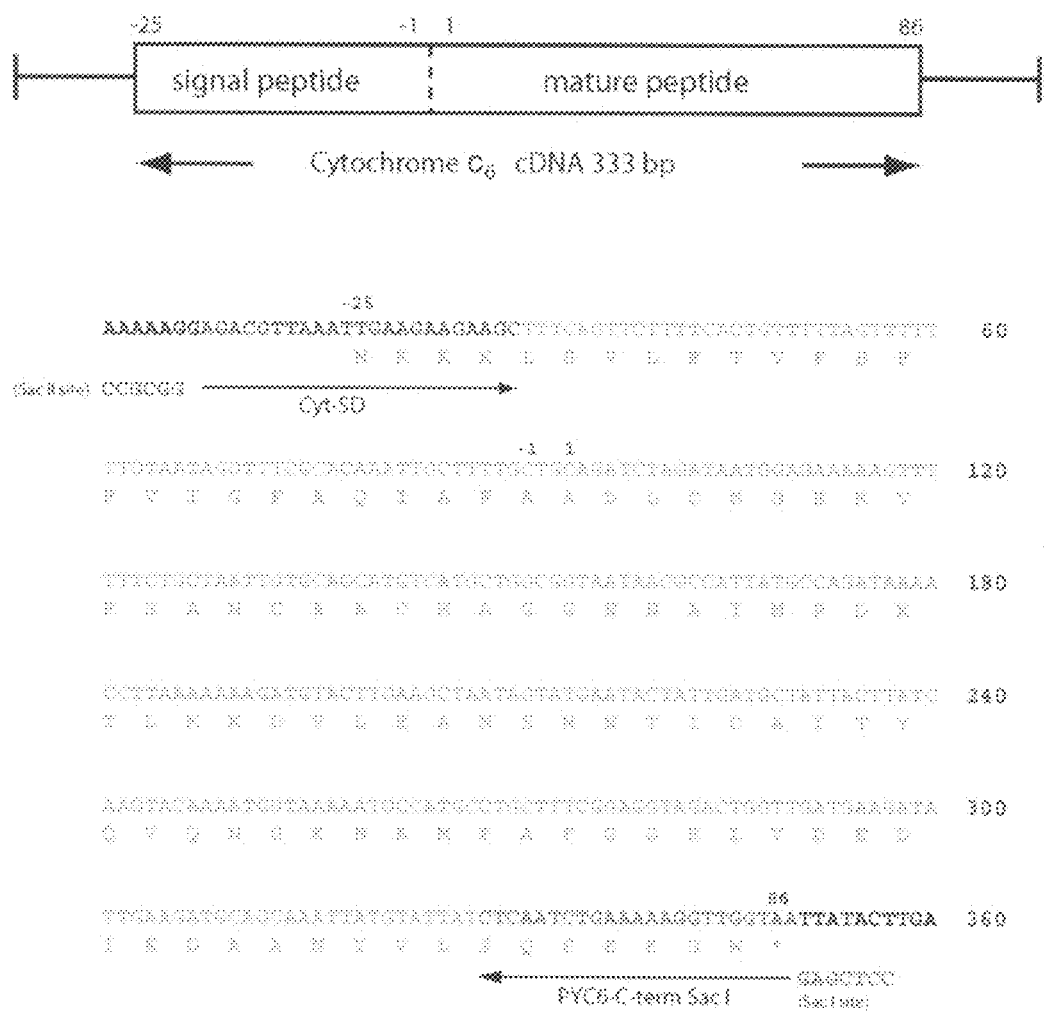
FIG. 4 is a view showing the nucleotide sequence (SEQ ID NO: 13) of the cDNA of *Porphyra yezoensis* cytochrome $c_6$ and a putative amino acid sequence (SEQ ID NO: 14).
Figure 5:
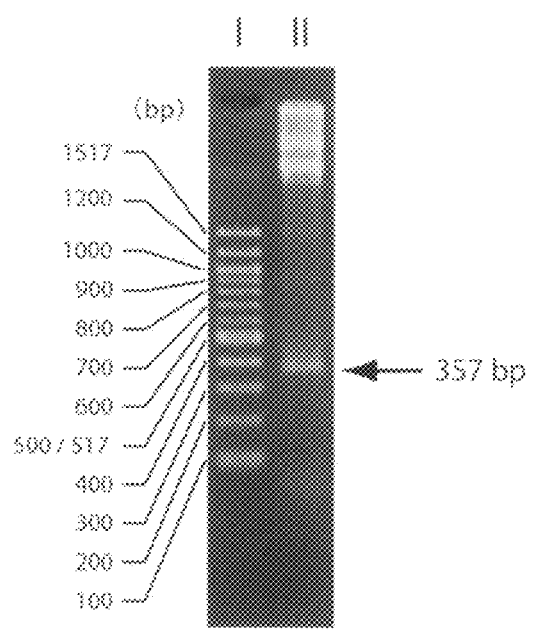
FIG. 5 is a view showing the results obtained by amplifying the mature protein region of a *Porphyra yezoensis* cytochrome $c_6$ gene by PCR.

Using a plasmid, into which a *P. yezoensis*-derived cytochrome $c_6$ gene (overall length) had been inserted, as a template, a cytochrome $c_6$ mature protein region (PYC6) gene was amplified by PCR (FIG. 4). Thereafter, the PCR product was subjected to 2% (w/v) agarose gel (TBE) electrophoresis. As a result, a single band could be confirmed around 357 bp (FIG. 5). This band was considered to be a PYC6 gene. Thus, this PYC6 gene was digested with two restriction enzymes (SacI and PstI), and the resultant was then subjected to 2% (w/v) agarose gel (TBE) electrophoresis. A band around 265 bp that was considered to be the PYC6 gene (having SacI and PstI sites) was extracted from the gel, and it was then subjected to phenol extraction and ethanol precipitation, so as to obtain a PYC6 gene having SacI and PstI sites.

(2) Addition of Peptide Gene Having Ability to Pass Through Chloroplast Envelope and Thylakoid Membrane to Cytochrome $c_6$ In this section, a peptide gene having ability to pass through a chloroplast envelope and a thylakoid membrane, which had been subjected to a treatment with the restriction enzymes BamHI and PstI and dephosphorylation (BAP treatment), was ligated to a *P. yezoensis*-derived cytochrome $c_6$ mature protein region gene, which had been treated with the restriction enzymes SacI and PstI. Thereafter, the ligated product was further ligated to a cloning vector (pBluescript (registered trade mark) II SK+), followed by subcloning. Thereafter, the nucleotide sequence of a cytochrome $c_6$ (sp+PYC6) to be introduced into a plant was confirmed. The following universal primers were used in DNA sequencing.

```
Universal FITC Forward primer (M13 Fw primer)
(2 pmol/µl)
                                        (SEQ ID NO: 9)
5'-CGC CAG GGT TTT CCC AGT CAC GAC-3'

Universal FITC Reverse primer (M13 Rv primer)
(2 pmol/µl)
                                       (SEQ ID NO: 10)
5'-GAG CGG ATA ACA ATT TCA CAC AGG-3'
```

(2-1) Preparation of Cytochrome $c_6$ Gene to be Introduced into Plant

A reaction solution with the following composition was prepared.

| | |
|---|---|
| Peptide gene having ability to pass through chloroplast envelope and thylakoid membrane (BAP-treated) | 4.0 µl |
| *P. yezoensis* cytochrome $c_6$ mature protein region gene | 4.0 µl |
| 10 × Ligation Buffer | 2.0 µl |
| 2 mg/ml BSA Solution | 2.5 µl |
| Enzyme Solution ($T_4$ DNA Ligase) | 1.0 µl |
| Distilled water | 6.5 µl |
| Total volume | 20.0 µl |

The prepared reaction solution was incubated in a low temperature incubator (16° C.) overnight for a ligation reaction. Subsequently, alkaline phosphatase was added to the solution, so as to carry out dephosphorylation. A sample having the following composition was prepared in a 1.5 ml microcentrifuge tube, and it was then incubated at 37° C. for 3 hours, so as to carry out dephosphorylation using Bacterial Alkaline Phosphatase.

| | |
|---|---|
| Sample obtained after ligation | 10.0 µl |
| 10 × BAP Buffer | 10.0 µl |
| Bacterial Alkaline Phosphatase (BAP) | 2.5 µl |
| Distilled water | 77.5 µl |
| Total volume | 100.0 µl |

To the sample solution obtained after incubation, an equal amount of TE-saturated Phenol was added. Thereafter, the mixture was fully stirred using a vortex, followed by centrifugation at 14,000 rpm at 4° C. for 10 minutes. The water layer was transferred into a new 1.5 ml microcentrifuge tube, and 1/20 vol. of 3 M NaOAc (pH 5.2) and 2 vol. of 99.5% ethanol were then added thereto. After the mixture had been fully stirred, it was left at −20° C. for 30 minutes. Thereafter, the resultant was centrifuged at 14,000 rpm at 4° C. for 10 minutes, and the supernatant was then discarded. 500 µl of 75% ethanol was added to the precipitate, and the precipitate was then fully washed. The resultant was further centrifuged at 14,000 rpm at 4° C. for 5 minutes, and the supernatant was then discarded. The precipitate was air-dried to a certain extent, and it was then dissolved in 20 µl of TE.

(2-2) Preparation of Cloning Vector pBluescript (Registered Trade Mark) II SK+

A sample having the following composition was prepared in a 1.5 ml microcentrifuge tube, and it was then incubated at 37° C. for 5 hours, so that it was digested with the restriction enzyme SacI.

| | |
|---|---|
| pBluescript (registered trade mark) II SK + | 20 µl |
| 10 × L Buffer | 5 µl |
| SacI | 2 µl |
| Distilled water | 23 µl |
| Total volume | 50 µl |

To the sample solution obtained after incubation, an equal amount of TE-saturated Phenol was added. Thereafter, the mixture was fully stirred using a vortex, followed by centrifugation at 14,000 rpm at 4° C. for 10 minutes. The water layer was transferred into a new 1.5 ml microcentrifuge tube, and 1/20 vol. of 3 M NaOAc (pH 5.2) and 2 vol. of 99.5% ethanol were then added thereto. After the mixture had been fully stirred, it was left at −20° C. for 30 minutes. Thereafter, the resultant was centrifuged at 14,000 rpm at 4° C. for 10 minutes, and the supernatant was then discarded. 500 µl of 75% ethanol was added to the precipitate, and the precipitate was then fully washed. The resultant was further centrifuged at 14,000 rpm at 4° C. for 5 minutes, and the supernatant was then discarded. The precipitate was air-dried to a certain extent, and it was then dissolved in 20 µl of TE.

Subsequently, a sample having the following composition was prepared in a 1.5 ml microcentrifuge tube, and it was then incubated at 37° C. for 5 hours, so that it was digested with the restriction enzyme BamHI.

| | |
|---|---|
| Sample obtained after digestion with restriction enzyme | 20 µl |
| 10 × H Buffer | 5 µl |
| BamHI | 2 µl |
| Distilled water | 23 µl |
| Total volume | 50 µl |

After completion of the reaction, confirmation was carried out by 1.5% (w/v) agarose gel electrophoresis. 4 µl of a gel loading buffer was added to 20 µl of the obtained PCR product, and the obtained mixture was used as an electrophoretic sample. Electrophoresis was carried out at 100 V for 30 minutes using an electrophoresis buffer (1×TAE). After completion of the electrophoresis, the gel was stained with 0.1 mg/ml ethidium bromide for 7 minutes, and it was then decolorized with extra pure water for 10 minutes. The decolorized gel was placed on a UV transilluminator, and it was then photographed with a nonautomatic hooded instant camera. Thereafter, a band that was considered to be DNA of interest was cut out of 1.5% (w/v) agarose gel, and 100 µg of the gel was converted to 100 µl. 3 vol. of NaI solution was added to the gel, and the mixture was then fully stirred. Thereafter, the mixture was incubated at 55° C. for 5 minutes, so as to dissolve the gel. 10 µl of GLASSMILK was added to the resultant, and the mixture was intensively stirred at room temperature for 15 minutes, followed by centrifugation at 14,000 rpm at 4° C. for 5 seconds, so as to recover a precipitate. 300 µl of NEW WASH was added to the precipitate, and the mixture was then fully stirred. The resultant was centrifuged at 14,000 rpm at 4° C. for 5 seconds, so as to recover a precipitate. This operation was repeated 3 times, and the obtained precipitate was then dried. The dried precipitate was dissolved in 20 µl of distilled water. Thereafter, the obtained solution was transferred into a 0.5-ml assist PCR tube, and it was then centrifuged at 14,000 rpm at 4° C. for 30 seconds. The obtained supernatant was transferred into a new 1.5 ml microcentrifuge tube, and 1/20 vol. of 3 M NaOAc (pH 5.2) and 2 vol. of 99.5% ethanol were then added thereto. After the mixture had been fully stirred, it was left at −20° C. for 30 minutes. Thereafter, the resultant was centrifuged at 14,000 rpm at 4° C. for 10 minutes, and the supernatant was then discarded. 500 µl of 75% ethanol was added to the precipitate, and the precipitate was then fully washed. The resultant was further centrifuged at 14,000 rpm at 4° C. for 5 minutes, and the supernatant was then discarded. The precipitate was air-dried to a certain extent, and it was then dissolved in 20 µl of TE.

(2-3) Subcloning of Cytochrome $c_6$ Gene to be Introduced into Plants

The cytochrome $c_6$ gene was subcloned according to a known method (Hanahan, D., J. Mol. Biol., 166(4), 557-580 (1983); and Hiroki Nakayama et al., Bio Illustrated II, *Idenshi Kaiseki no Kiso* (Basic Gene Analyses), Shujunsha Co., Ltd., 83-88 (1996)).

The gene to be introduced into plants and a cloning vector were prepared such that they had the following compositions.

| | |
|---|---|
| Cytochrome $c_6$ to be introduced (after it was digested with BamHI and SacI) (BAP-treated) | 5 µl |
| pBluescript (registered trade mark) II SK+ (digested with BamHI and SacI) | 5 µl |
| 10 × Ligation Buffer | 2 µl |
| 2 mg/ml BSA Solution | 2.5 µl |
| Enzyme Solution ($T_4$ DNA Ligase) | 1 µl |
| Distilled water | 4.5 µl |
| Total volume | 20 µl |

The prepared reaction solution was incubated in a low temperature incubator (16° C.) overnight for a ligation reaction. *Escherichia coli* was transformed as follows. First, 150 µl of competent cells (DH5α) were melted on ice to a certain extent, and 4 µl of the ligated reaction solution was then gently added thereto. The mixture was softly stirred with the tip of a chip, and it was then left on ice for 30 minutes. After it had left for 30 minutes, it was heat shocked at 42° C. for 20 seconds. Thereafter, the resultant was left at rest on ice for 3 minutes. Thereafter, each of 100 µl of and 50 µl of cell mass solutions (Vector:Insert=1:1, and 1:3) was applied on the entire surface of an LB-Ampicillin-X-Gal-IPTG plate, using a cell inoculation loop, and it was then cultured at 37° C. overnight.

(2-4) Preparation of Plasmid by Alkaline SDS Method

The alkaline SDS method was carried out according to known means (Weiss. B, et al., J. Biol. Chem., 243, 4543-4555 (1968); and Birnboim, H. C., Methods Enzymol., 100, 243 (1983)). That is to say, a cell mass solution was subjected to a shaking culture in 3 ml of LB-Amplicillin liquid medium at 200 rpm at 37° C. for 16 hours, and it (1.5 ml each) was then dispensed into a 1.5 ml microcentrifuge tube, followed by centrifugation at 6,000 rpm at 4° C. for 10 minutes. Thereafter, the supernatant was eliminated by aspiration with an aspirator. 100 µl of Solution I (50 mM glucose-25 mM Tris-HCl (pH 8.0)-10 mM EDTA) was added to the precipitate (cell mass), and the obtained mixture was fully stirred with a vortex. Thereafter, 200 µl of Solution II was added thereto, and the obtained solution was stirred by gently turning it over. The solution was left at room temperature for 5 minutes, and 150 µl of Solution III (0.2 N NaOH-1% SDS) was further added thereto. The obtained mixture was left on ice for 30 minutes, and 100 µl of chloroform was then added thereto, followed by centrifugation at 14,000 rpm at 4° C. for 10 minutes. Thereafter, the supernatant was recovered in a new tube, and a double volume of 99.5% ethanol was then added thereto. The obtained mixture was stirred by gently turning it over, and it was then left at room temperature for 15 minutes. Thereafter, 500 µl of 70% ethanol was added to the reaction solution, and the obtained mixture was then centrifuged at 14,000 rpm at 4° C. for 10 minutes. The obtained precipitate was dried with TOMY MICRO Vac for 3 to 5 minutes, and it was then dissolved in 20 µl of TE.

In order to confirm that DNA of interest had been incorporated into the obtained plasmid, a sample having the following composition was prepared in a 1.5 ml microcentrifuge tube. It was then incubated at 37° C. for 120 minutes, so that it was digested with the restriction enzymes SacI and BamHI.

| | |
|---|---|
| Plasmid DNA | 5.0 µl |
| 10 × L Buffer | 2.0 µl |
| SacI | 0.5 µl |
| BamHI | 0.5 µl |
| 1 mg/ml RNase A | 0.5 µl |
| Distilled water | 11.5 µl |
| Total volume | 20.0 µl |

After completion of the reaction, confirmation was carried out by 2% (w/v) agarose gel electrophoresis. 2 µl of a gel loading buffer was added to 10 µl of the obtained PCR product, and the obtained mixture was used as an electrophoretic sample. Electrophoresis was carried out at 100 V for 30 minutes using an electrophoresis buffer (1×TBE). After completion of the electrophoresis, the gel was stained with 0.1 mg/ml ethidium bromide for 7 minutes, and it was then decolorized with extra pure water for 10 minutes. The decolorized gel was placed on a UV transilluminator, and it was then photographed with a nonautomatic hooded instant camera. As a result, with respect to only the sample into which the DNA of interest had been incorporated, 100 µl out of the remaining cell mass solution (1.5 ml) obtained after completion of the culture in 3 ml of LB-Ampicillin liquid medium was inoculated into 5 ml of LB-Ampicillin liquid medium, followed by a shaking culture at 200 rpm, at 37° C. for 16 hours.

(2-5) Preparation of Plasmid with Qiagen Spin Miniprep Kit

A cell mass solution obtained by the culture in 5 ml of LB-Ampicillin liquid medium was centrifuged at 6,000 rpm at 4° C. for 10 minutes, and the supernatant was then eliminated by aspiration with an aspirator. 250 µl of Buffer P1 included with the kit (QIAGEN Spin Miniprep Kit (250) (QIAGEN)) was added to the precipitate (cell mass), and it was fully suspended therein.

It is to be noted that the QIAGEN Spin Miniprep Kit (250) (QIAGEN) comprises a Collection tube, a QIA prep Spin Column, Buffer P1, Buffer P2, Buffer N3, Buffer PB, Buffer PE, and Buffer EB.

250 µl of Buffer P2 was added to the above suspension, and the obtained mixture was stirred by gently turning it over, until the solution became homogeneous. Thereafter, 350 µl of Buffer N3 was further added to the solution, and the obtained mixture was stirred by gently turning it over, followed by centrifugation at 13,000 rpm at 4° C. for 10 minutes. The obtained supernatant was transferred into a QIA prep spin column, which had previously been set in a Collection tube, and it was then centrifuged at 13,000 rpm at 4° C. for 1 minute. The filtrate accumulated in the Collection tube was discarded, and 500 µl of Buffer PB was then added to the QIA prep spin column, followed by centrifugation at 13,000 rpm at 4° C. for 1 minute. Thereafter, the filtrate was discarded again.

750 µl of Buffer PE was further added to the QIA prep spin column, followed by centrifugation at 13,000 rpm at 4° C. for 1 minute. Thereafter, the filtrate was discarded. Centrifugation was again carried out at 13,000 rpm at 4° C. for 1 minute, and only the QIA prep spin column was transferred to a new 1.5 ml microcentrifuge tube. 50 µl of Buffer EB was added to the center of the QIA prep spin column, and it was then left at room temperature for 1 minute, followed by centrifugation at 13,000 rpm at 4° C. for 1 minute. The obtained filtrate was defined as a plasmid sample.

In order to confirm that DNA of interest had been incorporated into the obtained plasmid, a sample having the following composition was prepared in a 1.5 ml microcentrifuge tube, and it was then incubated at 37° C. for 120 minutes, so that it was digested with the restriction enzymes SacI and BamHI.

| | |
|---|---|
| Plasmid DNA | 5.0 µl |
| 10 × L Buffer | 2.0 µl |
| SacI | 0.5 µl |
| BamHI | 0.5 µl |
| Distilled water | 12.0 µl |
| Total volume | 20.0 µl |

After completion of the reaction, confirmation was carried out by 2% (w/v) agarose gel electrophoresis. 2 µl of a gel loading buffer was added to 10 µl of the obtained PCR product, and the obtained mixture was used as an electrophoretic sample. Electrophoresis was carried out at 100 V for 30 minutes using an electrophoresis buffer (1×TBE). After completion of the electrophoresis, the gel was stained with 0.1 mg/ml ethidium bromide for 7 minutes, and it was then decolorized with extra pure water for 10 minutes. The decolorized gel was placed on a UV transilluminator, and it was then photographed with a nonautomatic hooded instant camera. Herein, a sample, into which the DNA of interest had been incorporated and wherein unity had been confirmed, was defined as a sequence sample.

(2-6) Determination of Nucleotide Sequence According to Dideoxy Method

Nucleotide sequences were determined by a known method using an autosequencer (Sanger, F., Sanger, F., Determination of nucleotide sequence in DNA., Science, 214, 1205-1210 (1981)). After determination of such nucleotide sequences, data were analyzed using analysis software, GENETYX-MAC.

(2-7) Results

An sp gene, which had been subjected to digestion with two restriction enzymes (BamHI and PstI) and dephosphorylation (BAP treatment), was ligated to a PYC6 gene, which had been digested with two restriction enzymes (SacI and PstI). The ligated product was treated with BAP again, and the resultant was then subjected to phenol extraction and ethanol precipitation, so as to produce a cytochrome $c_6$(sp+PYC6) gene to be introduced into plants.

Figure 6:
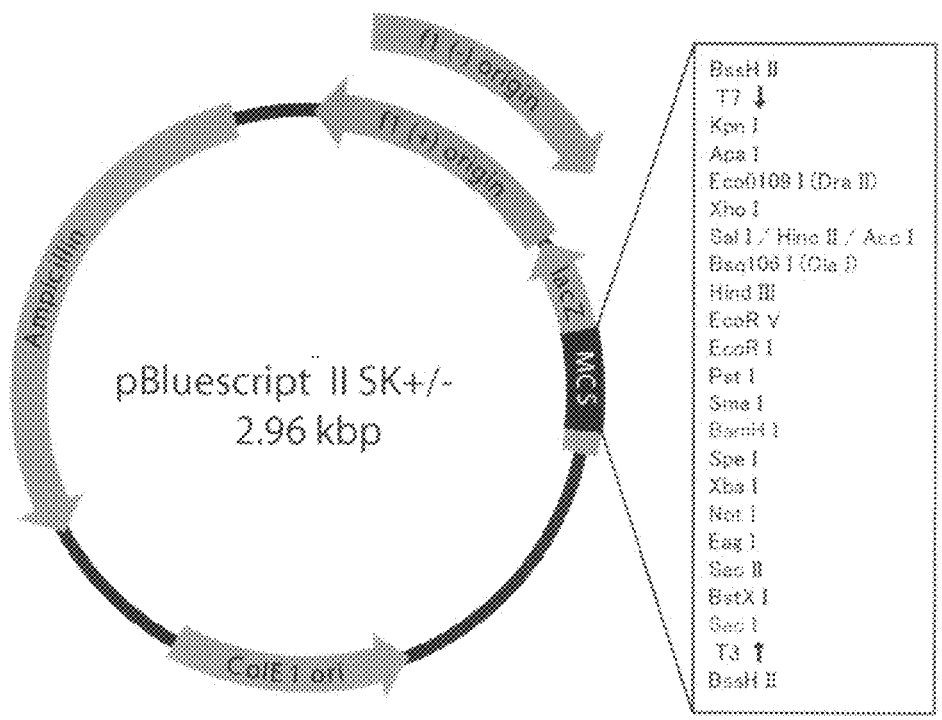
FIG. 6 is a view showing a pBluescript II SK+/− vector used in construction of a cytochrome $c_6$ gene to be introduced into plants.
Figure 7:
FIG. 7 is a view showing the nucleotide sequence (SEQ ID NO: 15) of a gene that is formed by fusing a signal peptide of plastocyanin derived from *Arabidopsis thaliana* with a mature protein region of cytochrome $c_6$ derived from *Porphyra yezoensis*, and a putative amino acid sequence (SEQ ID NO: 16).

In order to determine the nucleotide sequence of this sp+PYC6 gene, the gene was ligated to a cloning vector (pBluescript II SK+ (FIG. 6)), which had been digested with two restriction enzymes (BamHI and SacI), followed by subcloning. Thereafter, the resultant was sequenced by the dideoxy method, so as to determine the entire nucleotide sequence (474 bp) of the sp+PYC6 gene (FIG. 7).

The sequence results of the sp+PYC6 gene were compared with those of the known sp gene or PYC6 gene. As a result, it was revealed that the sequence of the sp+PYC6 gene was completely identical to that of the known sp gene or PYC6 gene, with the exception that T (thymine) at position 103 in the signal peptide sequence had been mutated to A (adenine). In addition, restriction enzyme sites added into primer sequences were also confirmed (FIG. 7). Due to the thus confirmed nucleotide mutation, the encoded amino acid Ser was converted to Thr. However, their properties and molecular weights were similar, and such conversion had no influence upon the secondary structure α-helix, etc.). Thus, since such conversion has no influence upon the function as a signal peptide, such as membrane transfer, this sample (sp+PYC6) was used in the subsequent experiment.

(3) Production of Expression Vector for Cytochrome $c_6$ to be Introduced into Plants In the present example, a cytochrome $c_6$(sp+PYC6) gene to be introduced into plants, whose nucleotide sequence had been confirmed, was inserted into an expression vector pBI121, so as to construct an expression vector (pBI cyt $c_6$) used for cytochrome $c_6$ to be introduced into plants.

(3-1) Preparation of Plant Expression Vector pBI121

A sample having the following composition was prepared in 1.5 ml microcentrifuge tube, and it was then incubated at 37° C. for 5 hours, so that it was digested with the restriction enzyme SacI.

| | |
|---|---|
| pBI121 | 20 µl |
| 10 × L Buffer | 5 µl |
| SacI | 2 µl |
| Distilled water | 23 µl |
| Total volume | 50 µl |

To the sample solution obtained after the incubation, an equal amount of TE-saturated Phenol was added. Thereafter, the mixture was fully stirred using a vortex, followed by centrifugation at 14,000 rpm at 4° C. for 10 minutes. The water layer was transferred into a new 1.5 ml microcentrifuge tube, and ½₀ vol. of 3 M NaOAc (pH 5.2) and 2 vol. of 99.5% ethanol were then added thereto. After the mixture had been fully stirred, it was left at −20° C. for 30 minutes. Thereafter, the resultant was centrifuged at 14,000 rpm at 4° C. for 10 minutes, and the supernatant was then discarded. 500 µl of 75% ethanol was added to the precipitate, and the precipitate was then fully washed. The resultant was further centrifuged at 14,000 rpm at 4° C. for 5 minutes, and the supernatant was then discarded. The precipitate was air-dried to a certain extent, and it was then dissolved in 20 µl of TE.

Subsequently, a sample having the following composition was prepared in a 1.5 ml microcentrifuge tube. The sample was then incubated at 37° C. for 5 minutes, so that it was digested with the restriction enzyme BamHI.

| | |
|---|---|
| Sample obtained after digestion with restriction enzyme | 20 µl |
| 10 × H Buffer | 5 µl |
| BamHI | 2 µl |
| Distilled water | 23 µl |
| Total volume | 50 µl |

After completion of the reaction, confirmation was carried out by 1.5% (w/v) agarose gel electrophoresis. 4 µl of a gel loading buffer was added to 20 µl of the obtained PCR product, and the obtained mixture was used as an electrophoretic sample. Electrophoresis was carried out at 100 V for 30 minutes using an electrophoresis buffer (1×TAE). After completion of the electrophoresis, the gel was stained with 0.1 mg/ml ethidium bromide for 7 minutes, and it was then decolorized with extra pure water for 10 minutes. The decolorized gel was placed on a UV transilluminator, and it was then photographed with a nonautomatic hooded instant camera. Thereafter, a band that was considered to be DNA of interest was cut out of 1.5% (w/v) agarose gel, and 100 µg of the gel was converted to 100 µl. 3 vol. of NaI solution was added to the gel, and the mixture was then fully stirred. Thereafter, the mixture was incubated at 55° C. for 5 minutes, so as to dissolve the gel. 10 µl of GLASSMILK was added to the resultant, and the mixture was intensively stirred at room temperature for 15 minutes, followed by centrifugation at 14,000 rpm at 4° C. for 5 seconds, so as to recover a precipitate. 300 µl of NEW WASH was added to the precipitate, and the mixture was then fully stirred. The resultant was centrifuged at 14,000 rpm at 4° C. for 5 seconds, so as to recover a precipitate. This operation was repeated 3 times, and the obtained precipitate was then dried. The dried precipitate was dissolved in 20 µl of distilled water. Thereafter, the obtained solution was transferred into a 0.5-ml assist PCR tube, and it was then centrifuged at 14,000 rpm at 4° C. for 30 seconds. The obtained supernatant was transferred into a new 1.5 ml microcentrifuge tube, and ⅟₂₀ vol. of 3 M NaOAc (pH 5.2) and 2 vol. of 99.5% ethanol were then added thereto. After the mixture had been fully stirred, it was left at −20° C. for 30 minutes. Thereafter, the resultant was centrifuged at 14,000 rpm at 4° C. for 10 minutes, and the supernatant was then discarded. 500 µl of 75% ethanol was added to the precipitate, and the precipitate was then fully washed. The resultant was further centrifuged at 14,000 rpm at 4° C. for 5 minutes, and the supernatant was then discarded. The precipitate was air-dried to a certain extent, and it was then dissolved in 20 µl of TE.

(3-2) Preparation of Cytochrome $c_6$ Expression Vector (pBI cyt $c_6$) Used for Expression in Plants The cytochrome $c_6$(sp+PYC6) gene to be introduced, which had been produced above, was used to prepare a reaction solution having the following composition.

| | |
|---|---|
| sp + PYC6 gene (after digestion with BamHI and SacI) (BAP-treated) | 4.0 µl |
| pBI121 (after digestion with BamHI and SacI) | 8.0 µl |
| 10 × Ligation Buffer | 2.0 µl |
| 2 mg/ml BSA Solution | 2.5 µl |
| Enzyme Solution ($T_4$ DNA Ligase) | 1.0 µl |
| Distilled water | 2.5 µl |
| Total volume | 20.0 µl |

The prepared reaction solution was incubated in a low temperature incubator (16° C.) overnight for a ligation reaction.

The results are shown below.

The sp+PYC6 gene (which had been digested with BamHI and SacI and had been treated with BAP), whose nucleotide sequence had been confirmed, was ligated to a plant expression vector (pBI121), which had been digested with two restriction enzymes (BamHI and SacI), so as to prepare a cytochrome $c_6$ expression vector (pBI cyt $c_6$) to be introduced into plants.

EXAMPLE 2

Production of Transgenic Plant (Cytochrome $c_6$-Introduced *Arabidopsis thaliana*)

(1) Preparation of *Agrobacterium tumefaciens* Used in Plant Infection (1-1) Preparation of Cytochrome $c_6$ Expression Vector (pBI cyt $c_6$)-Introduced *Escherichia coli*

In the present example, *Escherichia coli* HB101 used as a host was transformed with a plant expression vector (pBI cyt $c_6$), into which a cytochrome $c_6$ gene to be introduced into plants had been inserted. Thereafter, several colonies were selected, and they were then cultured in 3 ml of LB-Kanamycin liquid medium. A plasmid was prepared by the alkaline SDS method, so as to confirm construction of the vector and the presence or absence of transformation of the host *Escherichia coli* HB101.

*Escherichia coli* was transformed as follows. First, 150 µl of competent cells (HB101) were melted on ice to a certain extent, and 4 µl of the ligated reaction solution was then gently added thereto. The mixture was softly stirred with the tip of a chip, and it was then left on ice for 30 minutes. After it had left for 30 minutes, it was heat shocked at 42° C. for 20 seconds. Thereafter, the resultant was left at rest on ice for 3 minutes. Thereafter, each of 100 µl of and 50 µl of cell mass solutions was applied on the entire surface of an LB-Kanamycin plate, using a cell inoculation loop, and it was then cultured at 37° C. overnight.

After completion of the culture, 20 clones were randomly picked up from transformants (colonies), and the thus obtained colonies were then inoculated into 3 ml of LB-Kanamycin medium, and they were then subjected to a shaking culture at 200 rpm at 37° C. for 16 hours. Thereafter, the cultured cell mass solution (1.5 ml each) was then dispensed into a 1.5 ml microcentrifuge tube, followed by centrifugation at 6,000 rpm at 4° C. for 10 minutes. Thereafter, the supernatant was eliminated by aspiration with an aspirator. 100 µl of Solution I (the above-mentioned) was added to the precipitate (cell mass), and the obtained mixture was fully stirred with a vortex. Thereafter, 200 µl of Solution II (0.2 N NaOH-1% SDS) was added thereto, and the obtained solution was stirred by gently turning it over. The solution was left at room temperature for 5 minutes, and 150 µl of Solution III (the above-mentioned) was further added thereto. The obtained mixture was left on ice for 30 minutes, and 100 µl of chloroform was then added thereto, followed by centrifugation at 14,000 rpm at 4° C. for 10 minutes. Thereafter, the supernatant was recovered in a new tube, and a double volume of 99.5% ethanol was then added thereto. The obtained mixture was stirred by gently turning it over, and it was then left at room temperature for 15 minutes. Thereafter, 500 µl of 70% ethanol was added to the reaction solution, and the obtained mixture was then centrifuged at 14,000 rpm at 4° C. for 10 minutes. The obtained precipitate was dried with TOMY MICRO Vac for 3 to 5 minutes, and it was then dissolved in 20 µl of TE.

In order to confirm that DNA of interest had been incorporated into the obtained plasmid, a sample having the following composition was prepared in a 1.5 ml microcentrifuge tube, and it was then incubated at 37° C. for 120 minutes, so that it was digested with the restriction enzymes BamHI and SacI.

| | |
|---|---|
| Plasmid DNA | 5.0 µl |
| 10 × L Buffer | 2.0 µl |
| BamHI | 0.5 µl |
| SacI | 0.5 µl |
| 1 mg/ml RNase A | 0.5 µl |
| Distilled water | 11.5 µl |
| Total volume | 20.0 µl |

After completion of the reaction, confirmation was carried out by 1.5% (w/v) agarose gel electrophoresis. 2 µl of a gel loading buffer was added to 10 µl of the obtained PCR product, and the obtained mixture was used as an electrophoretic sample. Electrophoresis was carried out at 100 V for 30 minutes using an electrophoresis buffer (1×TAE). After completion of the electrophoresis, the gel was stained with 0.1 mg/ml ethidium bromide for 7 minutes, and it was then decolorized with extra pure water for 10 minutes. The decolorized gel was placed on a UV transilluminator, and it was then photographed with a nonautomatic hooded instant camera.

The results are shown below.

Figure 8:
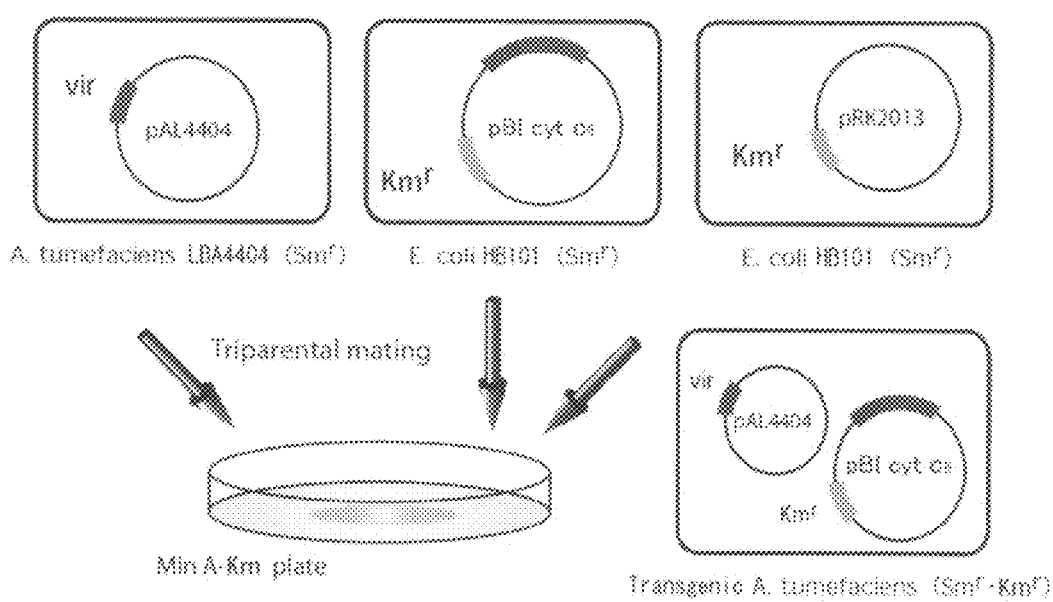
FIG. 8 is a schematic diagram showing a method of transforming *Agrobacterium tumefaciens* by triparental mating.

*Escherichia coli* HB101 used as a host was transformed with a cytochrome $c_6$ expression vector (pBI cyt $c_6$) used for expression in plants (FIG. 8). Thereafter, 20 clones were randomly picked up from transformants (colonies). As a result, in 3 out of the 20 clones, a single band could be confirmed around the size (474 bp) that was considered to be an sp+PYC6 gene. Thus, it was revealed that the sp+PYC6 gene had been inserted into this plasmid. The *Escherichia coli* HB101 having this plasmid was used in the subsequent experiment.

(1-2) Preparation and Selection of Transgenic *Agrobacterium tumefaciens*

In this section, triparental mating was carried out to prepare *Agrobacterium tumefaciens* used as a host that was necessary for introduction of a gene of interest into a higher plant *A. thaliana*. Thereafter, several colonies were selected from the obtained transformants, and they were then cultured in 3 ml of LB-Kanamycin liquid medium, followed by preparation of a plasmid by the alkaline SDS method, so as to confirm the presence or absence of transformation of the host *Agrobacterium*.

(1-2-1) Culture of Various Types of Strains (a) *Agrobacterium tumefaciens* (LBA4404) *pAL4404 maintenance A glycerol stock solution of the above strain was applied in a line drawing manner on the entire surface of a YEP-Streptomycin agar medium (plate) (30 µg/ml Streptomycin), using a platinum loop. It was then cultured at 30° C. for approximately 40 hours. After completion of the culture, a colony was picked up, and it was then subjected to a shaking culture in 5 ml of YEP-Streptomycin (30 µg/ml Streptomycin) medium at 200 rpm at 30° C. for 30 hours.

(b) *Escherichia coli* (HB101) *pRK2013 maintenance

A glycerol stock solution of the above strain was applied in a line drawing manner on the entire surface of an LB-Kanamycin agar medium (plate) (40 µg/ml Kanamycin), using a platinum loop. It was then cultured at 37° C. for 16 hours. After completion of the culture, a colony was picked up, and it was then subjected to a shaking culture in 5 ml of LB-Kanamycin (40 µg/ml Kanamycin) medium at 200 rpm at 37° C. for 16 hours.

(c) *Escherichia coli* (HB101) *pBI cyt $c_6$ maintenance

A glycerol stock solution of the above strain was applied in a line drawing manner on the entire surface of an LB-Kanamycin agar medium (plate) (40 µg/ml Kanamycin), using a platinum loop. It was then cultured at 37° C. for 16 hours. After completion of the culture, a colony was picked up, and it was then subjected to a shaking culture in 5 ml of LB-Kanamycin (40 µg/ml Kanamycin) medium at 200 rpm at 37° C. for 16 hours.

(1-2-2) Triparental Mating

Triparental mating was carried out according to a known method (Atsushi Komamine & Koji Nomura, "*Seibutsu Kagaku Jikken Ho* 41 (Biochemical Experimental methods 41)," *Syokubutsu Saibo Kogaku Nyumon* (Introduction of Plant Cell Technology), Japan Scientific Societies Press, 298-302 (1998)). That is, each of 3 types of strain solutions (strains having *A. tumefaciens* (LBA4404)*pAL4404, *E. coli* (HB101)*pBI cyt $c_6$, and *E. coli* (HB101)*pRK2013), which had been subjected to a shaking culture in 5 ml of YEP-Sm. liquid medium or LB-Km. liquid medium, was centrifuged at 5,000 rpm at 4° C. for 5 minutes. Thereafter, the supernatant was eliminated by aspiration with an aspirator. For washing, the liquid medium (YEP medium or LB medium) that had been used in the culture was added to the precipitate (cell mass), and the obtained mixture was fully stirred. Thereafter, the resultant was centrifuged again at 5,000 rpm at 4° C. for 5 minutes. After completion of the centrifugation, the cell mass was dissolved in 3 ml of the liquid medium used in the culture (YEP medium or LB medium). Subsequently, 30 µl of each cell mass solution was dropped on a Min A-Kanamycin agar medium (plate) such that it was laminated thereon. It was then left at rest, so that it was cultured at 30° C. for 3 days. After completion of the culture, a cell mass growing from the Min A-Kanamycin agar medium (plate) as a minimal medium was all scraped off using a platinum loop, and the thus obtained cell mass was then dissolved in 200 µl of 10 mM $MgSO_4$. Thereafter, the cell mass solution was applied in a line drawing manner on the entire surface of a Min A-Kanamycin agar medium (plate) again using a platinum loop, and it was then cultured at 30° C. for 3 days. After completion of the culture, a colony was picked up, and it was then subjected to a shaking culture in 5 ml of YEP-Kanamycin (40 µg/ml Kanamycin) medium at 200 rpm at 30° C. for 40 hours.

(1-2-3) Preparation of Ti Plasmid by Alkaline SDS Method

The cell mass solution (1.5 ml each), which had been subjected to a shaking culture in 5 ml of YEP-Kanamycin (40 µg/ml Kanamycin) liquid medium at 200 rpm at 30° C. for 40 hours, was dispensed in a 1.5 ml microcentrifuge tube. Thereafter, the above cell mass solution was centrifuged at 5,000 rpm at 4° C. for 10 minutes, and the supernatant was then eliminated by aspiration with an aspirator. Thereafter, 1 ml of S-buffer was added to the precipitate (cell mass), and the obtained mixture was fully stirred using a vortex. The mixture was centrifuged at 8,000 rpm at 4° C. for 10 minutes, and the supernatant was then eliminated by aspiration with an aspirator.

S-buffer was prepared by weighing 13.512 g of $C_6H_{12}O_6$ (glucose (M.W.: 180.16)), adding 12.5 ml of 1 M Tris-HCl (pH 8.0) and 10 ml of 0.5M EDTA (pH 8.0) thereto, and adjusting the volume to 500 ml with extra pure water, followed by an autoclave treatment (121° C., 10 minutes).

100 µl of S-buffer and 5 µl of 10 mg/ml lysozyme were added to the precipitate again, and the obtained mixture was left at room temperature for 10 minutes. Thereafter, 200 µl of Solution II and 30 µl of TE-saturated Phenol were added thereto, and the obtained solution was stirred by gently turning it over. The solution was left at room temperature for 5 minutes, and 150 µl of Solution III was further added thereto. The obtained mixture was left at −20° C. for 15 minutes, and the resultant was then centrifuged at 12,000 rpm at 4° C. for 10 minutes. The water layer was transferred into a new 1.5 ml microcentrifuge tube, and 1/20 vol. of 3 M NaOAc (pH 5.2) and 2 vol. of 99.5% ethanol were then added thereto. After the mixture had been fully stirred, it was left at −20° C. for 30 minutes. Thereafter, the resultant was centrifuged at 14,000 rpm at 4° C. for 10 minutes, and the supernatant was then discarded. 500 μl of 75% ethanol was added to the precipitate, and the precipitate was then fully washed. The resultant was further centrifuged at 14,000 rpm at 4° C. for 5 minutes, and the supernatant was then discarded. The precipitate was air-dried to a certain extent, and it was then dissolved in 20 μl of TE.

1 ml of RNase A was added to the obtained plasmid, and the obtained mixture was then incubated at 37° C. for 90 minutes so as to conduct an RNase treatment. After completion of the reaction, confirmation was carried out by 1.5% (w/v) agarose gel electrophoresis. 2 μl of a gel loading buffer was added to 10 μl of the obtained PCR product, and the obtained mixture was used as an electrophoretic sample. Electrophoresis was carried out at 100 V for 30 minutes using an electrophoresis buffer (1×TAE). After completion of the electrophoresis, the gel was stained with 0.1 mg/ml ethidium bromide for 7 minutes, and it was then decolorized with extra pure water for 10 minutes. The decolorized gel was placed on a UV transilluminator, and it was then photographed with a nonautomatic hooded instant camera.

The following results were obtained. *A. tumefaciens* (LBA4404) was cultured in a YEP-Sm. Medium, and *E. coli* (HB101) was cultured in an LB-Km. medium. Thereafter, pBI cyt $c_6$ was introduced into *A. tumefaciens* (LBA4404) by triparental mating, so as to transform *A. tumefaciens* (LBA4404). Subsequently, 10 clones were randomly picked up from the transgenic *A. tumefaciens* strains, into which the Ti plasmid (pBI cyt $c_6$) had been introduced by triparental mating. Such colonies were cultured in 3 ml of YEP-Km. medium. Thereafter, a plasmid was prepared by the alkaline SDS method, and it was then subjected to 1% (w/v) agarose gel electrophoresis. As a result, in 1 clone, a band could be confirmed at a size (13.5 kbp) that was considered to be pBI cyt $c_6$. Thus, it was revealed that the Ti plasmid (pBI cyt $c_6$) had been introduced into the transgenic *A. tumefaciens*.

(2) Production of Transgenic Plant (Cytochrome $c_6$-Introduced *Arabidopsis thaliana*)

(2-1) Cultivation of *Arabidopsis thaliana*

Vermiculite was placed up to about 9 parts of a 7.5×7.5 round pot, which had well washed with water. Subsequently, 500 ml of a solution was prepared by 2,000 times diluting a HYPONex stock solution with water, and rock wools, which had been sliced into a thickness of approximately 1 cm with a cutter, were placed in the above solution. 3 rock wools, which had been well impregnated with water, were placed on each of the 7.5×7.5 round pots. A mesh used for the sink in the kitchen was cut into a size sufficient to cover the mouth of the pot, and it then well washed with water. Thereafter, the mouth of the pot was covered with the mesh, and it was then bound with a rubber band. Thereafter, a single seed was inseminated into each of such pots. After insemination of the seed, a low temperature treatment was carried out thereon at 4° C. for 3 days. After completion of the low temperature treatment, the pot was transferred into a light irradiation incubator used for the growth of plants, followed by cultivation under 22° C. for long day conditions.

After germination, water was given approximately once 2 days, and HYPONex that had been 1,000 times diluted was given as a liquid fertilizer approximately once a week. Seedlings were thinned out as appropriate. Approximately 3 weeks later, when plant bodies started to form flower buds, pinching was carried out, and the grown plant bodies were supported with bamboo skewers (supports). When the seeds have completely matured, they were collected. The collected seeds were preserved in a dry state.

(2-2) Infection of Plant Body with Transgenic *Agrobacterium tumefaciens*

Subsequently, in order to introduce into a higher plant *A. thaliana* (col-0), cytochrome $c_6$ (sp+PYC6 gene) to be introduced into plants, a transgenic plant was produced by a vacuum infiltration method, one of *Agrobacterium* methods (Bechtold, N., Pelletier, G., Methods in Molecular Biology, 82 (1998)). Specific procedures are as follows.

(2-2-1) Culture of *Agrobacterium tumefaciens*

A glycerol stock solution of the above strain was applied in a line drawing manner on the entire surface of a Min A-Km. agar medium (plate) (400 μg/ml Kanamycin), using a platinum loop. It was then cultured at 30° C. for 40 hours. After completion of the culture, a colony was picked up, and it was subjected to a shaking culture (pre-culture) in 10 ml of YEP-Km. (40 μg/ml Kanamycin) medium at 200 rpm at 30° C. for 30 hours. Thereafter, the total amount of the culture solution was added to 100 ml of new YEP-Km. (40 μg/ml Kanamycin) medium, and a shaking culture (main culture) was then carried out at 200 rpm at 30° C. for 30 hours.

(2-2-2) Cultivation of Plant Body, *Arabidopsis thaliana* (col-0)

The following cultivation conditions were applied from insemination to collection of seeds of *A. thaliana* (col-0) used as a plant to be transformed.

Low temperature treatment: leaving at rest at 4° C. (dark place) for 3 days

Plant growth temperature: 22° C.

Light irradiation: long day conditions (100 μE $m^{-2}$ $s^{-1}$)

Liquid fertilizer: HYPONeX (1/1,000 times diluted)

In the case of a wild-type strain, it germinated 7 days after insemination (including 3 days for the low temperature treatment), and the plant formed flower buds approximately 20 days after germination. Thereafter, the plant was subjected to a pinching treatment. 5 or 6 days later, lateral branches began to extend, and at the same time, the opening of a first flower and fructication started. When green pods became light brown and began to split in the longitudinal direction, seeds were collected. Approximately 50 seeds were collected from a single pod. The collected seeds were preserved in a dry state until the time of insemination.

(2-2-3) Infection of Plant Body

A plant body *Arabidopsis thaliana* (col-0) used to be infected, was cultivated according to the method described in the section (2-2-2) above, and it was allowed to grown until it began to form flower buds. Thereafter, when foliage began to be derived from the stem, the plant was pinched, so as to eliminate flowers that had already opened and fructified. In this experiment, preparation of this plant body and preparation of the cell mass culture solution described in the section (2-2-1) were simultaneously carried out.

First, a Kimtowel was placed on a testing bench on which an infiltration operation was to be performed.

Subsequently, an *A. tumefaciens* culture solution was diluted at a magnification of about 2/3 with a suspension medium used in infiltration, and the diluted solution was then poured into a 1-L beaker. The beaker was set in an aspiration jar. Thereafter, a plant body of *A. thaliana*, which had been allowed to absorb a sufficient amount of water immediately before inoculation such that it did not aspirate an excessive amount of culture suspension, was then inoculated into a pot. Thereafter, the pot was immobilized upside-down on the beaker, so as to immerse the plant body in the culture suspension.

An *A. tumefaciens* culture solution having $OD_{600}$=1.2 to 1.5 was diluted at a magnification of about ⅔ with a suspension medium used in infiltration, so as to obtain $OD_{600}$=0.8, and the thus obtained *A. tumefaciens* culture solution was used in the vacuum infiltration method. In addition, as a result of examination about the vacuum infiltration time, such as 30 seconds, 1 minute, 5 minutes, and 10 minutes, it was found that 5 minutes was the most suitable as a time required for vacuum infiltration. That is, the longer such vacuum infiltration time, the poor the subsequent growth of the plant body that could be obtained. In the case of the treatment for 5 minutes, deterioration of the growth was not observed, and the number of flowers and the number of fructified pods (seeds) were not significantly different from those of a plant body that had been treated for 1 minute.

Subsequently, the plant body that had been immersed in the culture suspension was placed in the aspiration jar, and the pressure was then reduced using an aspirator. After completion of the depressurization, the plant body was removed from the aspiration jar, and a redundant culture suspension was wiped with a Kimtowel. The plant body was placed sideways on a plastic tray, and water was added dropwise to the edge thereof. Thereafter, the plastic tray was closed, and it was then left at 20° C. for 2 or 3 days (during this period, no water was given). Thereafter, the pot was raised, and it was then cultivated, as usual, in a light irradiation incubator used for the growth of plants at 22° C. under long day conditions. Water was given approximately once 2 days, and HYPONex that had been 1,000 times diluted was given as a liquid fertilizer approximately once a week. Seedlings were thinned out as appropriate. Approximately 3 weeks later, when plant bodies started to form flower buds, pinching was carried out, and the grown plant bodies were supported with bamboo skewers (supports). When the seeds have completely matured, they were collected. The collected seeds were preserved in a dry state.

EXAMPLE 3

Analysis of Introduction of Cytochrome $c_6$ Gene into Transgenic Plant Body and Expression Thereof (1) Analysis of Gene Introduced into Genomic DNA by PCR Method In the present example, genomic DNA was extracted from transgenic *Arabidopsis thaliana*. Using the genomic DNA as a template, PCR was carried out. Introduction of a gene into the plant body was confirmed based on the presence or absence of amplification of the introduced gene.

(1-1) Extraction of Genomic DNA from Transformant

Approximately 2 or 3 leaves of transgenic *Arabidopsis thaliana* were placed in a mortar that had previously been cooled, and liquid nitrogen was rapidly added thereto. Thereafter, the plant body was homogenized until it became a powder state. Thereafter, the powder sample was placed in a 1.5 ml microcentrifuge tube, followed by weighing. 1 ml of a solution obtained by adding 2-mercaptoethanol to Wash buffer to a final concentration of 0.5% was added to the weighed sample, and the mixture was fully blended. The mixture was centrifuged at 12,500 rpm at 4° C. for 10 minutes, and the supernatant was then discarded. 300 µl of a solution obtained by adding 2-mercaptoethanol to Solution I to a final concentration of 1% was added thereto, and the obtained mixture was fully blended using a vortex. Subsequently, 30 µl of 1% $NaBH_4$ and 150 µl of Solution II were added to the resultant, and the obtained mixture was stirred using a vortex for several seconds. The resultant solution was incubated at 50° C. for 10 minutes, and 100 µl of Solution III-A and 120 µl of Solution III-B included with ISOPLANT II (NIPPON GENE) were then added to the solution. The obtained solution was left on ice for 10 minutes.

The resultant was centrifuged at 12,500 rpm at 4° C. for 10 minutes, and the water phase was recovered. Thereafter, 2 vol. of 99.5% ethanol was added thereto, and the mixture was immediately centrifuged at 8,000 rpm at room temperature for 1 hour. Thereafter, the supernatant was discarded. 1 ml of 70% ethanol was further added thereto, and the mixture was then centrifuged at 8,000 rpm at room temperature for 1 minute. Thereafter, the supernatant was discarded. The precipitate was air-dried to a certain extent, and it was then dissolved in 50 µl of TE. 1 µl of 1 mg/ml RNase A was added to the solution, and the mixture was then incubated at 37° C. for 30 minutes. Thereafter, in order to confirm extraction of genomic DNA, 1 µl of a gel loading buffer was added to 5 µl of the obtained genomic DNA, and using λHindIII as a marker, 1.5% (w/v) agarose gel electrophoresis was carried out. The electrophoresis was carried out using an electrophoresis buffer (1×TAE) at 100 V for 30 minutes. After completion of the electrophoresis, the gel was stained with 0.1 mg/ml ethidium bromide for 7 minutes, and it was then decolorized with extra pure water for 10 minutes. The decolorized gel was placed on a UV transilluminator, and it was then photographed with a nonautomatic hooded instant camera.

After the presence of genomic DNA had been confirmed by the electrophoresis, the genomic DNA solution was 100 times diluted, and UV was then measured with a spectrophotometer, so as to measure the concentration of the genomic DNA. Based on the calculated concentration, the concentration of genomic DNA solution was adjusted to 10 ng/µl, and it was the used in the subsequent experiment.

(1-2) PCR

PCR was carried out according to a known method (Sambrook, J. D., W. Russell, Molecular Cloning: a Laboratory Manual, 3rd edn. Cold Spring Harbor Laboratory Press, Cold Spring Harbor, N.Y.).

A reaction solution having the following composition was prepared in a 0.5-ml assist PCR tube.

| | |
|---|---|
| Template (genomic DNA (10 ng)) | 1.0 µl |
| Primer (1) (10 pmol/µl) | 1.0 µl |
| Primer (3) (10 pmol/µl) | 1.0 µl |
| 10 × Ex Taq buffer ($Mg^{2+}$ plus) ($Mg^{2+}$ concentration: 20 mM) | 2.5 µl |
| dNTP Mixture (2.5 mM each) | 2.0 µl |
| DMSO | 1.25 µl |
| Distilled water | 16.1 µl |
| TaKaRa Ex Taq (5 U/µl) | 0.15 µl |
| Total volume | 25.0 µl |

15 µl of mineral oil was laminated on this reaction solution. Thereafter, the reaction was carried out using PTC-100™ Programmable Thermal Controller.

The following primers were used.

```
Primer (3) ATP-NA1 Bam (10 pmol/µl) (31 mer,
GC-Cont.: 54.8%)
                                    (SEQ ID NO: 11)
5'-GGA TCC ATG GCC GCA ATT ACA TCA GCT ACC G-3'

Primer (1) PYC6-C-term SacI (10 pmol/µl) (30mer,
GC-Cont.: 43.3%)
                                    (SEQ ID NO: 7)
5'-GGA GCT CTT ACC AAC CTT TTT CAG ATT GAG-3'

Universal FITC Forward primer (M13 Fw primer)
(2 pmol/µl)
                                    (SEQ ID NO: 9)
5'-CGC CAG GGT TTT CCC AGT CAC GAC-3'

Universal FITC Reverse primer (M13 Rv primer)
(2 pmol/µl)
                                    (SEQ ID NO: 10)
5'-GAG CGG ATA ACA ATT TCA CAC AGG-3'
```

The reaction was carried out under conditions of (94° C.-48 seconds, 64° C.-48 seconds, and 72° C.-1 minute 24 seconds)×31 cycles.

After completion of the reaction, confirmation was carried out by 2% (w/v) agarose gel electrophoresis. 2 µl of a gel loading buffer was added to 10 µl of the obtained PCR product, and the obtained mixture was used as an electrophoretic sample. Electrophoresis was carried out at 100 V for 30 minutes using an electrophoresis buffer (1×TBE). After completion of the electrophoresis, the gel was stained with 0.1 mg/ml ethidium bromide for 7 minutes, and it was then decolorized with extra pure water for 10 minutes. The decolorized gel was placed on a UV transilluminator, and it was then photographed with a nonautomatic hooded instant camera.

(1-3) Gel Extraction of PCR Product

A band that was considered to be DNA of interest was cut out of 2% (w/v) agarose gel, and it was then minced as finely as possible. The gel was placed in Amicon Ultra free (registered trade mark) DA, and it was then centrifuged at 7,300 rpm at 4° C. for 10 minutes. After completion of the centrifugation, Ultra free MC (a column portion on the upper side) was removed, and to the eluted solution, an equal amount of TE-saturated Phenol was added. Thereafter, the mixture was fully stirred using a vortex, followed by centrifugation at 14,000 rpm at 4° C. for 10 minutes. The water layer was transferred into a new 1.5 ml microcentrifuge tube, and ¹⁄₂₀ vol. of 3 M NaOAc (pH 5.2) and 2 vol. of 99.5% ethanol were then added thereto. After the mixture had been fully stirred, it was left at −20° C. for 30 minutes. Thereafter, the resultant was centrifuged at 14,000 rpm at 4° C. for 10 minutes, and the supernatant was then discarded. 500 µl of 75% ethanol was added to the precipitate, and the precipitate was then fully washed. The resultant was further centrifuged at 14,000 rpm at 4° C. for 5 minutes, and the supernatant was then discarded. The precipitate was air-dried to a certain extent, and it was then dissolved in 20 µl of TE. In order to confirm that the DNA of interest had been uniquely extracted and purified in this solution, 2% (w/v) agarose gel electrophoresis was carried out. 2 µl of a gel loading buffer was added to 10 µl of the obtained sample, and electrophoresis was carried out using an electrophoresis buffer (1×TBE) at 100 V for 30 minutes. After completion of the electrophoresis, the gel was stained with 0.1 mg/ml ethidium bromide for 7 minutes, and it was then decolorized with extra pure water for 10 minutes. The decolorized gel was placed on a UV transilluminator, and it was then photographed with a nonautomatic hooded instant camera.

(1-4) Subcloning of PCR Product

The subcloning of the PCR product was carried out according to a known method (Hanahan, D., J. Mol. Biol., 166(4), 557-580 (1983); and Hiroki Nakayama et al., Bio Illustrated II, *Idenshi Kaiseki no Kiso* (Basic Gene Analyses), Shujunsha Co., Ltd., 83-88 (1996)).

The PCR product and other components were prepared to have the following composition.

|  | Insert:Vector (1:1) | Insert:Vector (3:1) |
|---|---|---|
| PCR products | 0.5 µl | 1.5 µl |
| pGEM (registered trade mark) - T Easy Vector | 0.5 µl | 0.5 µl |
| 2 × Lapid Ligation Buffer | 5.0 µl | 5.0 µl |
| T₄ DNA Ligase | 1.0 µl | 1.0 µl |
| Distilled water | 3.0 µl | 3.0 µl |
| Total volume | 10.0 µl | 10.0 µl |

The prepared reaction solution was incubated in a low temperature incubator (16° C.) overnight for a ligation reaction. *Escherichia coli* was transformed as follows. First, 150 µl of competent cells (DH5α) were melted on ice to a certain extent, and 4 µl of the ligated reaction solution was then gently added thereto. The mixture was softly stirred with the tip of a chip, and it was then left on ice for 30 minutes. After it had left for 30 minutes, it was heat shocked at 42° C. for 20 seconds. Thereafter, the resultant was left at rest on ice for 3 minutes. Thereafter, each of 100 µl of and 50 µl of cell mass solutions (Vector:Insert=1:1, and 1:3) was applied on the entire surface of an LB-Ampicillin-X-Gal-IPTG plate, using a cell inoculation loop, and it was then cultured at 37° C. overnight.

(1-5) Preparation of Plasmid According to Alkaline SDS Method

In this section, a plasmid was prepared in the same manner as that described in Example 1 (2-4).

(1-6) Preparation of Plasmid Using Qiagen Spin Miniprep Kit

In this section, a plasmid was prepared in the same manner as that described in Example 1 (2-5).

(1-7) Determination of Nucleotide Sequence According to Dideoxy Method

In this section, a nucleotide sequence was determined by the same method as that described in Example 1 (2-6). The following results were obtained.

Figure 9:
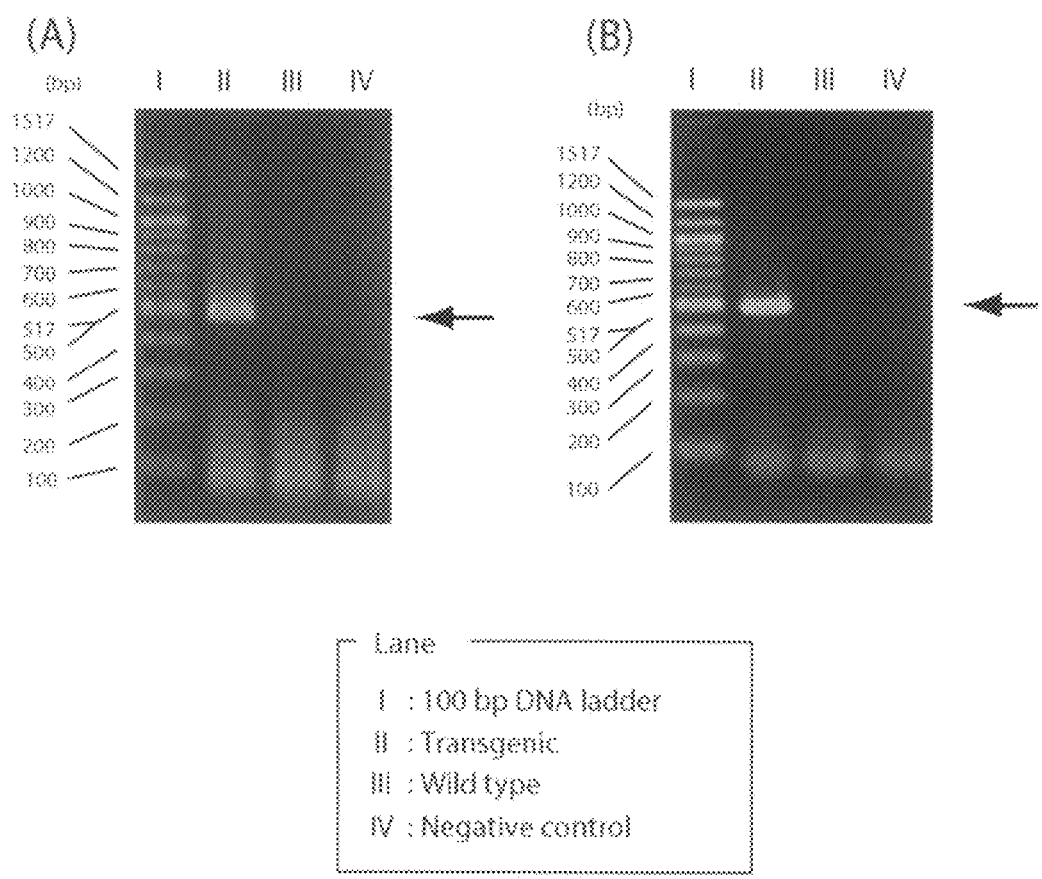
FIG. 9 is a view showing the results obtained by performing electrophoresis on a cytochrome $c_6$ gene introduced into a plant, which has been specified by PCR. (A) shows the results obtained using genomic DNA as a template, and (B) shows the results obtained using total RNA as a template.

High purity genomic DNA was extracted from 2 or 3 leaves of transgenic *A. thaliana*, using ISOPLANT II. In order to confirm the presence or absence of introduction of a cytochrome c₆ gene used to be introduced into plants, using the genomic DNA solution as a template, a gene of interest was amplified by PCR. Thereafter, the PCR product was subjected to 2% (w/v) agarose gel (TBE) electrophoresis. As a result, a single band was confirmed around 474 bp (FIG. 9). In order to determine the nucleotide sequence of the amplified gene, after gel extraction, subcloning was carried out. Thereafter, the amplified gene was sequenced by the dideoxy method, so as to determine the entire nucleotide sequence consisting of 474 bp. The sequence results were compared with the known sp gene sequence and PYC6 gene sequence, using GENETYX-MAC. As a result, as with the introduced gene, the determined nucleotide sequence was completely identical to those of the above genes with the exception that T (thymine) at position 103 in the signal peptide gene sequence was substituted with A (adenine). From the above results, it was revealed that an sp+PYC6 gene had been introduced into the plant body (*A. thaliana*).

(2) Analysis of Expression Gene in Total RNA According to RT-PCR Method

In the present section, total RNA was extracted from transgenic *Arabidopsis thaliana*, and RT-PCR was carried out using the total RNA as a template. Thereafter, based on the presence or absence of amplification of the introduced gene, expression of the gene in the plant body was confirmed.

```
Primer (3) ATP-NA1 Bam (10 pmol/µl) (31 mer,
GC-Cont.: 54.8%)
                                            (SEQ ID NO: 8)
5'-GGA TCC ATG GCC GCA ATT ACA TCA GCT ACC G-3'

Primer (1) PYC6-C-term SacI (10 pmol/µl) (30 mer,
GC-Cont.: 43.3%)
                                            (SEQ ID NO: 7)
5'-GGA GCT CTT ACC AAC CTT TTT CAG ATT GAG-3'

Universal FITC Forward primer (M13 Fw primer)
(2 pmol/µl)
                                            (SEQ ID NO: 6)
5'-CGC CAG GGT TTT CCC AGT CAC GAC-3'

Universal FITC Reverse primer (M13 Rv primer)
(2 pmol/µl)
                                            (SEQ ID NO: 7)
5'-GAG CGG ATA ACA ATT TCA CAC AGG-3'
```

(2-1) Extraction of Total RNA from Transformant

Total RNA was extracted from a transformant using a commercially available kit (RNeasy Plant Mini Kit (QIAGEN)) in accordance with an instruction included therewith.

(2-2) PCR

PCR was carried out according to a known method (Sambrook, J. D., W. Russell, Molecular Cloning: a Laboratory Manual, 3rd edn. Cold Spring Harbor Laboratory Press, Cold Spring Harbor, N.Y.).

A reaction solution having the following composition was prepared in a 0.5-ml assist PCR tube.

| | |
|---|---|
| Template (total RNA (10 ng)) | 1.0 µl |
| Primer (1) (10 pmol/µl) | 1.0 µl |
| Primer (3) (10 pmol/µl) | 1.0 µl |
| 10 × Ex Taq buffer ($Mg^{2+}$ plus) ($Mg^{2+}$ concentration: 20 mM) | 2.5 µl |
| dNTP Mixture (2.5 mM each) | 2.0 µl |
| DMSO | 1.25 µl |
| Distilled water | 16.1 µl |
| TaKaRa Ex Taq (5 U/µl) | 0.15 µl |
| Total volume | 25.0 µl |

15 µl of mineral oil was laminated on the above reaction solution. Thereafter, a reaction was carried out using PTC-100™ Programmable Thermal Controller.

After completion of the reaction, confirmation was carried out by 2% (w/v) agarose gel electrophoresis. 2 µl of a gel loading buffer was added to 10 µl of the obtained PCR product, and the obtained mixture was used as an electrophoretic sample. Electrophoresis was carried out at 100 V for 30 minutes using an electrophoresis buffer (1×TBE). After completion of the electrophoresis, the gel was stained with 0.1 mg/ml ethidium bromide for 7 minutes, and it was then decolorized with extra pure water for 10 minutes. The decolorized gel was placed on a UV transilluminator, and it was then photographed with a nonautomatic hooded instant camera.

(2-3) Gel Extraction of PCR Product

In this section, gel extraction of the PCR product was carried out in the same manner as that described in Example 3 (1-3).

(2-4) Subcloning of PCR Product

In this section, the subcloning of the PCR product was carried out by the same method as that described in Example 3 (1-4).

(2-5) Preparation of Plasmid According to Alkaline SDS Method

In this section, the alkaline SDS method was carried out according to known means by the same method as that described in Example 1 (2-4) (Weiss. B, et al., J. Biol. Chem., 243, 4543-4555 (1968); Birnboim, H. C., Methods Enzymol., 100, 243 (1983)).

(2-6) Preparation of Plasmid Using Qiagen Spin Miniprep Kit

In this section, a plasmid was prepared using QIAGEN Spin Miniprep Kit by the same method as that described in Example 1 (2-5).

(2-7) Determination of Nucleotide Sequence According to Dideoxy Method

In this section, a nucleotide sequence was determined by the same method as that described in Example 1 (2-6) (Sanger, F., Sanger, F., Determination of nucleotide sequence in DNA., Science, 214, 1205-1210 (1981)).

(2-8) Results

The expressed total RNA was extracted from 2 or 3 leaves of a transgenic plant (PYC6-introduced plant) wherein introduction of the gene had been confirmed, using RNeasy Plant Mini Kit. In order to confirm the presence or absence of expression of an sp+PYC6 gene, using the total RNA solution as a template, a gene of interest was amplified by RT-PCR. Thereafter, the PCR product was subjected to 2% (w/v) agarose gel (TBE) electrophoresis. As a result, a single band was confirmed around 474 bp (FIG. 9). In order to determine the nucleotide sequence of the amplified gene, after gel extraction, subcloning was carried out. Thereafter, the amplified gene was sequenced by the dideoxy method, so as to determine the entire nucleotide sequence consisting of 474 bp. The sequence results were compared with the known sp gene sequence and PYC6 gene sequence, using GENETYX-MAC. As a result, as with the introduced gene, the determined nucleotide sequence was completely identical to those of the above genes with the exception that T (thymine) at position 103 in the signal peptide gene sequence was substituted with A (adenine). From the above results, it was considered that the sp+PYC6 gene had been expressed in the plant body (*A. thaliana*).

(3) Analysis of Expressed Protein According to Western Blotting Method

In this section, chloroplast was extracted from transgenic *Arabidopsis thaliana*. Thereafter, it was confirmed that the introduced cytochrome $c_6$ had been expressed in a chloroplast protein fraction obtained from the extracted chloroplast.

(3-1) Preparation of Chloroplast Fraction

A chloroplast fraction was prepared according to known means (Kenzo Nakamura et al., (edited), *Shokubutsu no Tanpakushitsu Jikken Protocol* (Plant Protein Experimental Protocols), *Saibo Kogaku Series* (Cell Technology Series), Vol. 9, Shujunsha Co., Ltd., 114-117 (1998)).

Approximately 5 to 6 g of transgenic *Arabidopsis thaliana* was placed in a mortar that had previously been cooled, and liquid nitrogen was rapidly added thereto. Thereafter, the plant body was homogenized until it became a powder state. Thereafter, 20 ml of disintegration buffer that had been cooled on ice was added to the powder sample, and the mixture was then fully stirred. Thereafter, the mixture was filtrated with 4 layers of Miracloth. The obtained filtrate was transferred into a 15-ml corning tube, and it was then centrifuged at 7,000 rpm at 4° C. for 15 seconds. Thereafter, the supernatant was carefully eliminated. 5 vol. of disintegration buffer was added to the precipitate, and they were blended so as to form a homogeneous solution. Thereafter, the obtained solution was gently laminated on a glass centrifuge tube, in which 10 ml of 30% Percoll had previously been placed. It was then centrifuged at 2,000 rpm at 4° C. for 3 minutes. After completion of the centrifugation, Percoll as a supernatant was eliminated, and the precipitate was mixed into 5 ml of disintegration buffer, until the obtained mixture became homogeneous. The mixture was centrifuged at 2,000 rpm, at 4° C. for 3 minutes, again. (This operation was repeated twice). Finally, the precipitate was dissolved in 1 ml of disintegration buffer, and the solution was defined as a chloroplast fraction.

(3-2) Western Blotting 1 ml of CelLytic P Plant Cell Lysis/Extraction reagent was added to the chloroplast fraction solution obtained in (3-1) above, and the obtained mixture was then centrifuged at 10,000 rpm at 4° C. for 10 minutes. The obtained supernatant was defined as a chloroplast protein extraction solution. 5 µl of a 1 µg/µl molecular weight standard marker, 5 µl of extra pure water, and the chloroplast protein extraction solution were added to a 1.5 ml microcentrifuge tube. To each tube, an equal amount of sample buffer was added, and the mixture was then fully stirred. The prepared tube was incubated at 40° C. for 30 minutes in a hot-water bath, and it was then used as an electrophoretic sample.

An anode electrode solution, a cathode electrode solution, and SDS-PAGE gel were set in an electrophoretic tank, and 20 µl of the electrophoretic sample was carefully applied in a well. Thereafter, the electrophoretic sample was electrophoresed up to the upper end of resolving gel at a constant voltage of 30 V, and the marker was electrophoresed up to approximately 5 mm from the lower end of the gel at a constant voltage of 100 V. During the electrophoresis, two filters were immersed in each of blotting buffers A, B, and C. The PVDF membrane was immersed in a small amount of methanol for 5 seconds and was then immersed in the blotting C solution. After completion of the electrophoresis, the gel was removed from the glass board, and it was then immersed in the blotting C solution for approximately 5 minutes. Two filters A, two filters B, the PVDF membrane, the gel, and two filters C were laminated in this order from the bottom of a semi-dry blotting device. After they had been laminated, transcription was conducted at a constant current of 60 mA for 90 minutes. Immediately after completion of the blotting, operations were conducted in the following orders, so as to carry out an antigen-antibody reaction.

(i) The PVDF membrane is immersed in TBS and is then shaken for 5 minutes (2 times);

(ii) It is immersed in 5% BSA in TBS and is then shaken from 1 hour to overnight;

(iii) It is immersed in TBS, and is then shaken for 5 minutes;

(iv) It is immersed in $1^{st}$-antibody, and is then shaken for 2 hours;

(v) It is immersed in TTBS, and is then shaken for 5 minutes (2 times);

(vi) It is immersed in $2^{nd}$-antibody, and is then shaken for 1 hour 30 minutes;

(vii) It is immersed in TTBS, and is then shaken for 5 minutes (2 times);

(viii) It is immersed in TBS, and is then shaken for 5 minutes (2 times);

(ix) It is immersed in a $2^{nd}$-antibody development reagent, and is then shaken for 20 minutes (light-blocked); and (x) It is washed with extra pure water.

(3-3) Results

Figure 10:
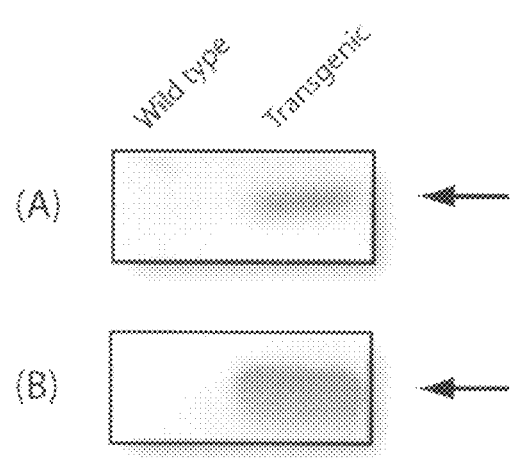
FIG. 10 is a view showing the results obtained by specifying by electrophoresis cytochrome $c_6$ that has been allowed to express in a plant. (A) shows the results obtained by CBB staining, and (B) shows the results of Western blotting, wherein cytochrome $c_6$ has been allowed to react with a cytochrome $c_6$ antibody.

A chloroplast fraction was separated from a PYC6-introduced plant by Percoll density gradient centrifugation. The obtained chloroplast proteins were electrophorestically screened by SDS-PAGE in terms of molecular weight. Subsequently, all of the separated proteins were transcribed onto a PVDF membrane, and an antigen-antibody reaction was carried out using a primary antibody (rabbit antibody) and an anti-rabbit antibody (secondary antibody) that recognized cytochrome $c_6$ derived from *P. yezoensis*. As a result, such an antigen-antibody reaction could be detected only in the PYC6-introduced plant (FIG. 10). From such results, it was revealed that PYC6 introduced into the PYC6-introduced plant was expressed in the chloroplast.

(4) Analysis of N-Terminal Amino Acid Sequence of Expressed Cytochrome $c_6$ Protein In this section, the N-terminal amino acid sequence of a PYC6 protein that exhibited an antigen-antibody reaction in (3) above was analyzed, and the presence or absence of the cleavage of a signal peptide was then confirmed.

1 ml of CelLytic P Plant Cell Lysis/Extraction reagent was added to the chloroplast fraction solution obtained in (3-1) above, and the obtained mixture was then centrifuged at 10,000 rpm at 4° C. for 10 minutes. The obtained supernatant was defined as a chloroplast protein extraction solution. 5 µl of a 1 µg/µl molecular weight standard marker, 5 µl of extra pure water, and the chloroplast protein extraction solution were added to a 1.5 ml microcentrifuge tube. To each tube, an equal amount of sample buffer was added, and the mixture was then fully stirred. The prepared tube was incubated at 40° C. for 30 minutes in a hot-water bath, and it was then used as an electrophoretic sample.

An anode electrode solution, a cathode electrode solution, and SDS-PAGE gel were set in an electrophoretic tank, and 20 µl of the electrophoretic sample was carefully applied in a well. Thereafter, the electrophoretic sample was electrophoresed up to the upper end of resolving gel at a constant voltage of 30 V, and the marker was electrophoresed up to approximately 5 mm from the lower end of the gel at a constant voltage of 100 V. During the electrophoresis, two filters were immersed in each of blotting buffers A, B, and C. The PVDF membrane was immersed in a small amount of methanol for 5 seconds and was then immersed in the blotting C solution. After completion of the electrophoresis, the gel was removed from the glass board, and it was then immersed in the blotting C solution for approximately 5 minutes. Two filters A, two filters B, the PVDF membrane, the gel, and two filters C were laminated in this order from the bottom of a semi-dry blotting device. After they had been laminated, transcription was conducted at a constant current of 60 mA for 90 minutes. After completion of the blotting, CBB staining and discoloration operation were conducted, and a protein portion of interest was cut into a size of 1 mm×5 mm, and the thus cut protein portion was then transferred into a 1.5 ml microcentrifuge tube. This was used as a sequence sample, and the amino acid sequence thereof was analyzed using Applied Biosystems Protein Sequencer 492.

The N-terminal amino acid sequence of a protein with a molecular weight of approximately 9.1 kDa having an antigen-antibody reaction with a PYC6 antibody obtained from the transgenic plant was analyzed by the Edman method. As a result, the sequence was found to be ADLDNGEKVF (SEQ ID NO: 12) from the $1^{st}$ residue on the N-terminus (please refer to the following table).

|  | Molecular mass (kDa) | N-terminal sequence |
|---|---|---|
| *P. yezoensis* cyt c$_6$ | 9.1 | ADLDNGEKVF |
| PYC6 | 9.1 | ADLDNGEKVF |

This sequence is completely identical to the N-terminal amino acid sequence of the mature protein region of PYC6. From this result, it was revealed that the signal peptide had been cleaved in the plant body, and that PYC6 precisely had passed through the chloroplast thylakoid membrane and had been expressed on the lumen side. That is to say, as a result of the analysis of the N-terminal amino acid sequence of the PYC6 protein in the obtained transformant, it was found that the above sequence was identical to the amino acid sequence of the mature region wherein a chloroplast transport signal had been cleaved. Thus, it could be confirmed that the sp+PYC6 gene was transcribed and translated, and was then transported to the chloroplast.

EXAMPLE 4

Measurement of Growth of Transgenic Plant and Observation of Phenotype (1) Growth Observation (Height, Root Length, and Leaf Size)

In this section, the growth of transgenic *Arabidopsis thaliana* after insemination was observed.

After the transgenic plant had been inseminated, the "height," "root length," and "leaf size" of the plant body were observed and measured every 10 days. As plant samples, 20 individual wild-type strains and 20 individual transgenic plants were prepared. The mean value was calculated, and a significant difference was then obtained by statistical processing.

As a result of observation of the growth (phenotype) of the PYC6-introduced plants, the height of such a plant was at maximum 1.9 times greater than that of the wild-type plant (WT) (40 days after insemination), and it was then 1.3 times greater than that of WT on the approximately 60$^{th}$ day (FIG. 11). The root length of such a PYC6-introduced plant was at maximum 1.35 times greater than that of WT (40 days after insemination), and it was then 1.17 times greater than that of WT on the approximately 60$^{th}$ day (FIG. 12). The leaf size of such a PYC6-introduced plant was at maximum 1.9 times greater than that of WT (40 days after insemination), and it was then 1.3 times greater than that of WT on the approximately 60$^{th}$ day (FIG. 13). It was considered that such phenomena occurred in such PYC6-introduced plants were brought on due to activation of a photosynthetic reaction extremely important for the growth of plants as a result of expression of PYC6 in the plant bodies. Thus, it was considered that the growth rate of the plant bodies was increased by the influence of such activation of a photosynthetic reaction.

(2) Measurement of Total Chlorophyll Amount

In this section, the total amount of chlorophyll was extracted from transgenic *Arabidopsis thaliana* using acetone, and it was then quantified.

Leaves of transgenic *Arabidopsis thaliana* were collected using a leaf punch, and they were then weighed. The sample was placed in a mortar that had previously been cooled, and liquid nitrogen was then rapidly added thereto. The mixture was homogenized until the plant body became a powder state. Thereafter, 80% acetone was added to the powder sample, so as to adjust the volume to 4 ml. The absorbance values at 663 nm and at 645 nm of the above solution were measured using a spectrophotometer UV-VISIBLE SPECTROPHOTOMETER.

The obtained absorbance values at 663 nm and at 645 nm were assigned into the following formula, so as to calculate the chlorophyll amount.

$$\text{Total chlorophyll amount (μg/ml)} = 8.02 \times ABS(663) + 20.21 \times ABS(645)$$

Figure 14:
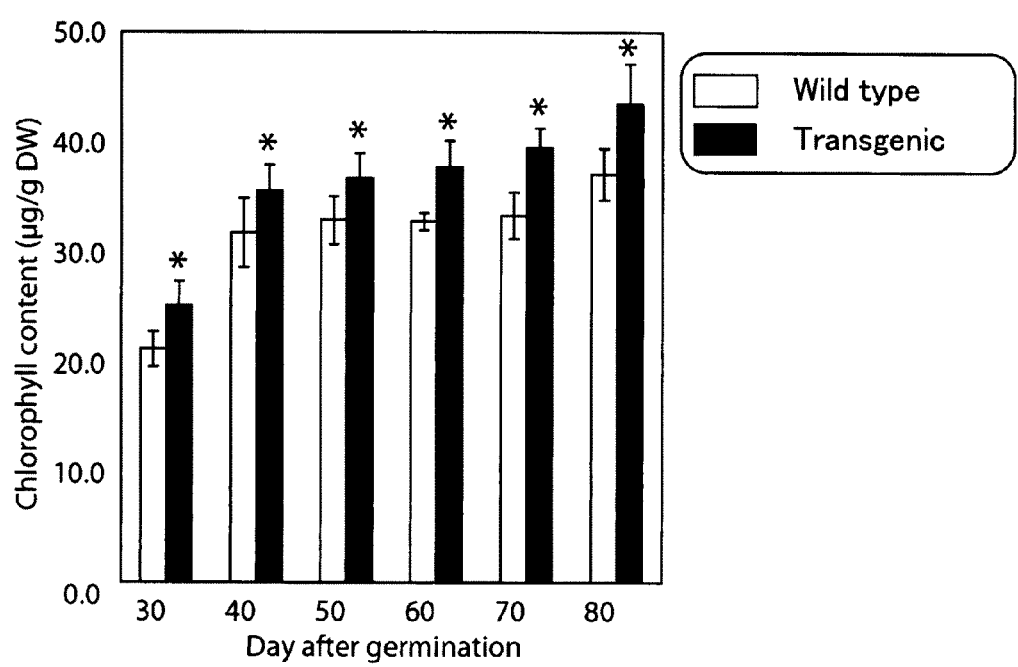
FIG. 14 is a view showing a change in the chlorophyll content of a wild type and in the chlorophyll content of transgenic *A. thaliana*, obtained 3 hours after light irradiation, which has been observed with the course of growing days.

As a result of the measurement of the chlorophyll amount in the PYC6-introduced plant, it was found that the chlorophyll amount in the PYC6-introduced plant was 1.1 to 1.2 times larger than that of WT during the period from 40 to 70 days after insemination (FIG. 14). It was considered that this was because a light reaction was activated by introduction of PYC6, and because an energetic substance (ATP) that was the thus increased final product of the light reaction was utilized in the synthesis of chlorophyll.

EXAMPLE 5

Measurement of Photosynthetic Activity of Transgenic Plant (1) Methods and Results In order to use as indicators of photosynthetic activity, an adenine nucleotide (ATP) content, an NADPH amount, carbon dioxide-assimilating ability, a starch amount, and a protein amount were measured by the following methods.

(1-1) Measurement of Total ATP Content

In the present example, total ATP was extracted from transgenic *Arabidopsis thaliana*, and it was then quantified by the luciferin-luciferase method.

Leaves of transgenic *Arabidopsis thaliana* had been weighed in advance. After weighing, the sample was placed in a mortar that had previously been cooled, and liquid nitrogen was then rapidly added thereto. The mixture was homogenized using a pestle until the plant body became a powder state. Thereafter, 2 ml of 0.25 M perchloric acid was added to the powder sample, and the obtained solution was then recovered in a 15-ml corning tube. The solution was centrifuged at 10,000 rpm at 4° C. for 10 minutes. Thereafter, the obtained supernatant was transferred into another 15-ml corning tube, and the pH was then adjusted to pH 7.0 with 1 N KOH. After the pH had been adjusted, the volume was adjusted to 5 ml with a 0.2 M phosphate buffer (pH 7.2), and the thus obtained solution was defined as an ATP extract.

100 μl of the ATP extract was prepared in a 1.5 ml microcentrifuge tube, and 20 μl of ENLITEN Luciferase/Luciferin Reagent was added thereto. 90 seconds after addition of the above agent, the integral of the luminescence intensity of the reaction solution was calculated for 10 seconds using a luminometer (GENE LIGHT 55). Thereafter, the ATP concentration in the solution was calculated from the obtained RLU value, and the ATP amount per weight of the plant was obtained from the obtained ATP concentration.

As a result, the total amount of ATP contained in the PYC6-introduced plant was increased by at maximum 1.93 times (60 days after insemination) (FIG. 15). It was considered that this was because *P. yezoensis* cyt c$_6$(PYC6) functioned as a new electron carrier, as well as plastocyanin functioning in the PYC6-introduced plant, so that electron transfer in a light reaction could be activated, and so that the amount of ATP as a final product was thereby increased.

(1-2) Measurement of Total NADPH Content

In the present example, total NADPH was extracted from transgenic *Arabidopsis thaliana*, and it was then quantified.

Transgenic *Arabidopsis thaliana* had been weighed in advance. Thereafter, 0.1 N NaOH was placed in the weighed transgenic plant, which had been heated with a hot bath at approximately 70° C., and the mixture was then disintegrated with a Polytron homogenizer. Thereafter, the resultant was transferred into an ice bath, and approximately 2 ml of 0.1 N HCl was added thereto. The obtained mixture was adjusted to pH 7.5 using a pH test paper. Subsequently, 0.1 ml of glycylglycine buffer (pH 7.5) was added to the mixture, and the obtained mixture was then fully stirred. Thereafter, the reaction solution was transferred into a measuring cylinder, and the liquid amount was then measured. After completion of the measurement, the solution was transferred into a 15-ml corning tube, and it was then centrifuged at 10,000 rpm at 4° C. for 20 minutes. After completion of the centrifugation, the supernatant was recovered in a 15-ml corning tube, and it was then cooled at −80° C. overnight. After the resultant had been dissolved, it was then centrifuged at 10,000 rpm at 4° C. for 20 minutes, and the resultant was then used in quantification.

100.0 μl of an NADPH extract, 346.0 μl of a 0.1 M glycylglycine buffer (pH 7.4), 200.0 μl of 0.2 M nicotinamide, 82.0 μl of 3.2 mg/ml phenazine methosulfate (PMS), 67.0 μl of 5 mg/ml thiazole blue, and 200 μl of glucose-6-dibasic sodium phosphate hydrate, were blended. The obtained mixture was set in a spectrophotometer U3310. Measurement was carried out at 570 nm at 25° C. A temperature control unit was installed in U3310, and the temperature thereof was set at 25° C. Thereafter, a change in the absorbance at 570 nm was measured every 30 seconds for 2 minutes, and based on differences in the obtained absorbance values, the amount of NADPH was calculated. Thereafter the amount of NADPH per weight of the plant was calculated from the above obtained value.

As a result, the total amount of NADPH contained in the PYC6-introduced plant was increased by 1.2 to 1.4 times on 40 to 70 days after insemination (FIG. 16). It was considered that this was because larger quantities of electrons were transferred into the PYC6-introduced higher plant than into a wild-type plant as a result of introduction of PYC6 into the higher plant, and because the amount of NADPH as a final product was thereby increased.

(1-3) Measurement of Carbon Dioxide-Assimilating Ability

In the present example, using leaves of transgenic *Arabidopsis thaliana*, carbon dioxide-assimilating ability was measured.

Such carbon dioxide-assimilating ability was measured using a $CO_2$ gas analyzer CIRAS-1 (manufactured by Koito Industries, Ltd.). In addition, the amount of carbon dioxide supplied was set at 350 ppm, and the measurement was then carried out under saturated light.

As a result, the carbon dioxide-assimilating ability of the PYC6-introduced plant was increased by at maximum 2.2 times (50 days after insemination) (FIG. 17). It was considered that this was because the amount of ATP and the amount of NADPH were increased by introduction of PYC6 into a higher plant, and a dark reaction (Calvin-Benson cycle) that utilized such energy was thereby activated, so that the carbon dioxide-assimilating ability was increased.

(1-4) Measurement of Starch Amount

In the present example, starch was extracted from transgenic *Arabidopsis thaliana*, and it was then quantified.

Plant leaves were collected and were then dried (70° C., 2 days). Approximately 5 mg of leaves were weighed out, and they were then placed in a mortar. Thereafter, 3 ml of 32% perchloric acid was added thereto, and the obtained mixture was then fully disintegrated with a pestle. Thereafter, all the obtained sample was placed in a test tube, and it was then left at rest at 20° C. for 20 minutes. Subsequently, the resultant was filtrated with a 6.0-cm Whatman GF/A grass fibre disk. Thereafter, 5 ml of an iodine solution was then added to the filtrate, and they were then well blended. The obtained mixture was left at rest at approximately 4° C. for 30 minutes. Thereafter, the resultant was filtrated with a 1.5-cm Whatman GF/A grass fibre disk, and the filter was then dried.

The dried filter was placed in a test tube, and 4 ml of 0.75 M sulfuric acid was then added thereto. The obtained mixture was incubated in a boiled water bath for 30 minutes. Thereafter, the supernatant was recovered, and color was developed therefrom according to the phenol sulfuric acid method. Thereafter, the absorbance at 485 nm was measured using a spectrophotometer.

As a result, the amount of starch contained in the PYC6-introduced plant was increased by 1.15 to 1.25 times for 40 to 70 days after insemination (FIG. 18). It was considered that this was because the $CO_2$-assimilating ability of the PYC6-introduced higher plant was increased by introduction of PYC6 into the higher plant, and the synthesis of starch was also promoted thereby.

(1-5) Measurement of Protein Amount

In the present example, protein was extracted from transgenic *Arabidopsis thaliana*, and it was then quantified by the Lowry method.

The weight of a plant body was measured and recorded. A suitable amount of plant body was placed in a mortar, and it was then sufficiently crushed with a pestle in the presence of liquid nitrogen. The temperature was returned to room temperature, and 2 ml of CelLytic P (manufactured by Sigma) was then added to 1 g of the plant body. The obtained mixture was sufficiently crushed with a pestle, and the resultant was then transferred into a test tube. The test tube was turned upside down at room temperature for 15 minutes, so that the mixture could be blended, followed by centrifugation. The obtained supernatant was defined as an extracted protein.

Subsequently, the following solutions were produced: Lowry A solution prepared by adding sodium carbonate to a 0.1 N sodium hydroxide solution resulting in 2%; Lowry B solution containing 0.5% copper sulfate pentahydrate and 1% sodium citrate; Lowry C solution consisting of a 1 N phenol solution; and Lowry D solution consisting of Lowry A solution and Lowry B solution. Thereafter, 1.0 ml of the Lowry D solution was added to 0.1 ml of the extracted protein solution, and the obtained mixture was then stirred using a vortex mixer, followed by incubation at 30° C. for 15 minutes. Subsequently, 0.1 ml of the Lowry C solution was added to the reaction solution, and the obtained mixture was rapidly stirred with a vortex mixer. The resultant was incubated at 30° C. for 30 minutes, and the absorbance at 770 nm was then measured.

As a result, the amount of protein contained in the PYC6-introduced plant was increased by at maximum 1.3 times (50 days after insemination) (FIG. 19). It was considered that this was because ATP and NADPH increased by introduction of PYC6 into a higher plant activated the synthesis of the protein.

(2) Consideration

By the present invention, it was found that the PYC6-introduced plant had a growth rate that was higher than that of WT. It was assumed that since ATP and NADPH contained in the PYC6-introduced plant were increased, *P. yezoensis* cyt $c_6$ acting as a newly introduced electron carrier functioned together with plastocyanin functioning in *A. thaliana*, resulting in two cycles of electron transfer in a light reaction. Accordingly, the amounts of ATP and NADPH as final products were increased, so that the growth of the plant as a whole could be activated. To date, an increase in the component amount of a land plant due to the reinforcement of enzymes associated with a dark reaction (Calvin-Benson cycle) has been studied. However, there have been no cases of activating a light reaction.

Moreover, to date, there have been no cases of introducing cyt $c_6$ into a plant to allow it function therein. Thus, the contents of the present invention are sufficiently applicable to other types of plants in the future. Accordingly, it can be said that the present invention has versatility and that it becomes a base for a method of promoting the growth of a useful plant, a plant production technique (fruit plants, foliage plants, real flowers, etc.), and the like. Furthermore, other types of metabolism are also activated utilizing ATP and NADPH increased in a plant body, and thus it was considered that the present invention was extremely effective for the field of a method of eliminating contaminants ($CO_2$, etc.).

INDUSTRIAL APPLICABILITY

The present invention provides a method of producing a novel higher plant having cytochrome $c_6$ in the thylakoid space of chloroplast. The present invention also provides a method of promoting the growth of a higher plant, a method of promoting the synthesis of ATP, NADPH, a starch, and a protein, and a method of promoting carbon fixation.

Moreover, the present invention further provides a signal peptide-added cytochrome $c_6$ protein that can be transported into the thylakoid space of chloroplast, a gene encoding the above protein, a recombinant vector comprising the above gene, a transformant comprising the above recombinant vector, and a transgenic higher plant which is obtained by introducing the above gene into the plant genome thereof.

SEQUENCE LISTING FREE TEXT

SEQ ID NO: 7-Primer
SEQ ID NO: 8-Primer
SEQ ID NO: 9-Primer
SEQ ID NO: 10-Primer
SEQ ID NO: 11-Primer

The invention claimed is:

1. A method of producing a higher plant having cytochrome $c_6$ in the thylakoid space of chloroplast, comprising
introducing a gene encoding a fused protein comprising a signal peptide consisting of 50 to 80 amino acid residues and a cytochrome $c_6$ protein into the genome of a higher plant,
wherein the cytochrome $c_6$ protein is from an algae selected from the group consisting of blue-green algae, bacillariophyta, chlorophyceae, and brown algae.

2. A method of promoting the growth of a higher plant, comprising
introducing a gene encoding a fused protein comprising a signal peptide consisting of 50 to 80 amino acid residues and a cytochrome $c_6$ protein into the genome of a higher plant,
expressing the gene under suitable conditions,
wherein the cytochrome $c_6$ is located in the thylakoid space of chloroplast
wherein the cytochrome $c_6$ protein is from an algae selected from the group consisting of blue-green algae, bacillariophyta, chlorophyceae, and brown algae.

3. A method of promoting the synthesis of at least one selected from the group consisting of the ATP, NADPH, starch, and protein of a higher plant, comprising
introducing a gene encoding a fused protein comprising a signal peptide consisting of 50 to 80 amino acid residues and a cytochrome $c_6$ protein into the genome of a higher plant,
expressing the gene under suitable conditions,
wherein the cytochrome $c_6$ is located in the thylakoid space of chloroplast
wherein the cytochrome $c_6$ protein is from an algae selected from the group consisting of blue-green algae, bacillariophyta, chlorophyceae, and brown algae.

4. A method of promoting carbon fixation by a higher plant, comprising
introducing a gene encoding a fused protein comprising a signal peptide consisting of 50 to 80 amino acid residues and a cytochrome $c_6$ protein into the genome of a higher plant,
expressing the gene under suitable conditions,
wherein the cytochrome $c_6$ is located in the thylakoid space of a chloroplast, wherein the cytochrome $c_6$ protein is from an algae selected from the group consisting of blue-green algae, bacillariophyta, chlorophyceae, and brown algae.

5. The method according to any one of claims 1 to 4, wherein the higher plant belongs to a plant family selected from the group consisting of solanaceae, gramineae, leguminosae, chenopodiaceae, rosaceae, asteraceae, liliaceae, caryophyllaceae, cucurbitaceae, convolvulaceae, amaranthaceae, bromeliaceae, cactaceae, aloaceae, and orchidaceae.

6. The method according to any one of claims 1 to 4, wherein the higher plant is a C4 plant, a Crassulacean acid metabolism plant, or a C3-C4 intermediate plant.

7. The method according to any one of claims 1 to 4, wherein the higher plant is a C3 plant selected from the group consisting of solanaceae, gramineae, leguminosae, chenopodiaceae, rosaceae, asteraceae, cucurbitaceae, convolvulaceae and orchidaceae.

* * * * *